(12) United States Patent
Smith et al.

(10) Patent No.: US 12,344,860 B2
(45) Date of Patent: *Jul. 1, 2025

(54) CELL-SUPPORT MATRIX HAVING NARROWLY DEFINED UNIFORMLY VERTICALLY AND NON-RANDOMLY ORGANIZED POROSITY AND PORE DENSITY AND A METHOD FOR PREPARATION THEREOF

(71) Applicant: Ocugen, Inc., Malvern, PA (US)

(72) Inventors: Robert Lane Smith, Palo Alto, CA (US); Laurence J. B. Tarrant, Northhampton, MA (US); Akihiko Kusanagi, Brookline, MA (US); Hans P. I. Claesson, Wayland, MA (US)

(73) Assignee: Ocugen, Inc., Malvern, PA (US)

( * ) Notice: Subject to any disclaimer, the term of this patent is extended or adjusted under 35 U.S.C. 154(b) by 831 days.

This patent is subject to a terminal disclaimer.

(21) Appl. No.: 17/156,062

(22) Filed: Jan. 22, 2021

(65) Prior Publication Data

US 2021/0246418 A1 Aug. 12, 2021

Related U.S. Application Data

(63) Continuation of application No. 16/706,372, filed on Dec. 6, 2019, now Pat. No. 10,900,017, which is a continuation of application No. 15/641,773, filed on Jul. 5, 2017, now abandoned, which is a continuation of application No. 14/577,610, filed on Dec. 19, 2014, now Pat. No. 9,701,940, which is a continuation of application No. 11/523,833, filed on Sep. 19, 2006, now Pat. No. 8,921,109.

(60) Provisional application No. 60/718,714, filed on Sep. 19, 2005.

(51) Int. Cl.
| | |
|---|---|
| *C12N 5/00* | (2006.01) |
| *A61F 2/30* | (2006.01) |
| *A61L 27/24* | (2006.01) |
| *A61L 27/38* | (2006.01) |
| *A61L 27/56* | (2006.01) |
| *C12N 5/077* | (2010.01) |
| *A61F 2/08* | (2006.01) |
| *A61F 2/38* | (2006.01) |

(52) U.S. Cl.
CPC ............ *C12N 5/0068* (2013.01); *A61L 27/24* (2013.01); *A61L 27/3817* (2013.01); *A61L 27/3843* (2013.01); *A61L 27/56* (2013.01); *C12N 5/0655* (2013.01); *A61F 2/08* (2013.01); *A61F 2002/30062* (2013.01); *A61F 2/30756* (2013.01); *A61F 2/3872* (2013.01); *A61F 2210/0004* (2013.01); *A61F 2310/00365* (2013.01); *A61L 2400/18* (2013.01); *A61L 2430/06* (2013.01); *A61L 2430/10* (2013.01); *C12N 2533/54* (2013.01); *C12N 2535/00* (2013.01)

(58) Field of Classification Search
CPC .... A61F 2002/30062; A61F 2210/0004; A61F 2310/00365; A61F 2/08; A61F 2/30756; A61F 2/3872; A61L 2400/18; A61L 2430/06; A61L 2430/10; A61L 27/24; A61L 27/3817; A61L 27/3843; A61L 27/56; C12N 2533/54; C12N 2535/00; C12N 5/0068; C12N 5/0655
See application file for complete search history.

(56) References Cited

U.S. PATENT DOCUMENTS 8,070,827 B2 * 12/2011 Shortkroff ............... A61L 27/38
                                                           623/23.72
8,106,008 B2 *  1/2012 Lynch ................... A61L 27/227
                                                              514/8.2

FOREIGN PATENT DOCUMENTS

WO    WO-2007057175 A2 *  5/2007   ......... A61L 27/3804

OTHER PUBLICATIONS

Guan J, Fujimoto KL, Sacks MS, Wagner WR "Preparation and Characterization of Highly Porous, Biodegradable Polyurethane Scaffolds for Soft Tissue Applications" Biomaterials. Jun. 2005 (ePub Dec. 8, 2004); 26(18): 3961-3971; PMID 15626443; doi: 10.1016/j.biomaterials.2004.10.018. (Year: 2004).*

Kozan NG, et al."Aligned Collagen Sponges with Tunable Pore Size for Skeletal Muscle Tissue Regeneration" J. Funct. Biomater. Oct. 24, 2023, 14(11), 533; 18 pages; doi: 10.3390/jfb14110533. (Year: 2023).*

* cited by examiner

*Primary Examiner* — Aaron J Kosar
(74) *Attorney, Agent, or Firm* — Don D. Cha; HDC Intellectual Property Law, LLP

(57) ABSTRACT

A cell-support matrix having narrowly defined uniformly vertically and non-randomly organized porosity and pore density and a method for preparation thereof. The matrix suitable for preparation of cellular or acellular implants for growth and de novo formation of an articular hyaline-like cartilage. A gel-matrix composite system comprising collagen-based matrix having a narrowly defined porosity capable of inducing hyaline-like cartilage production from chondrocytes in vivo and in vitro.

13 Claims, 16 Drawing Sheets

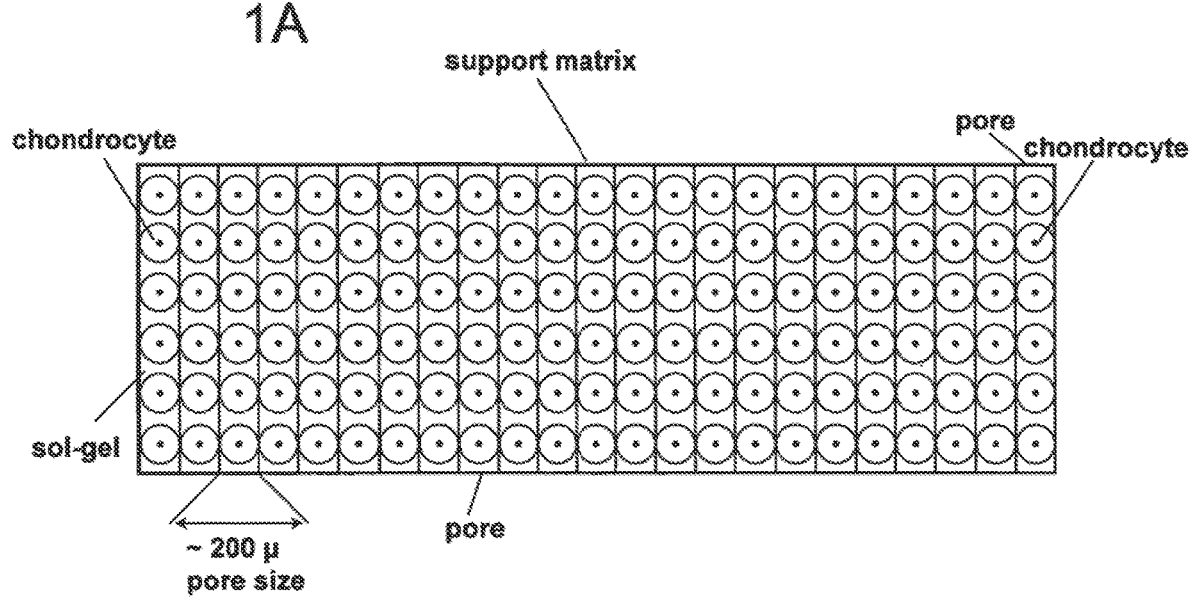
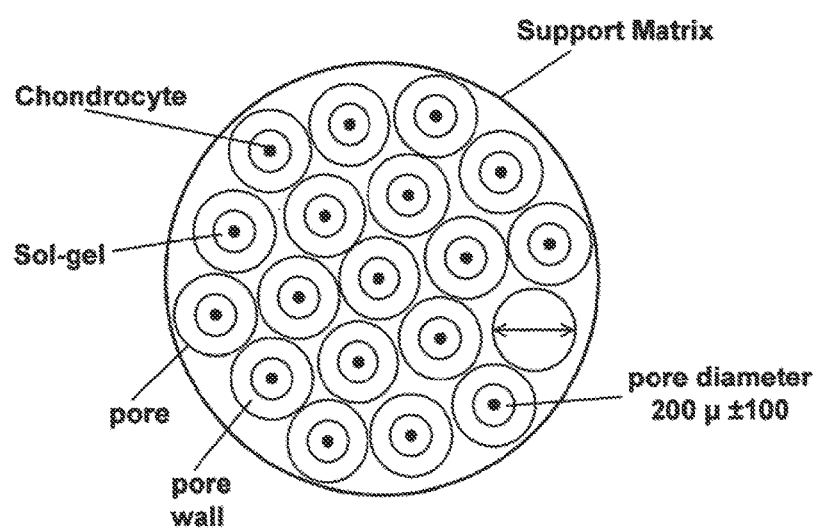
Fig. 1A-B

1C (Actual size)

1D
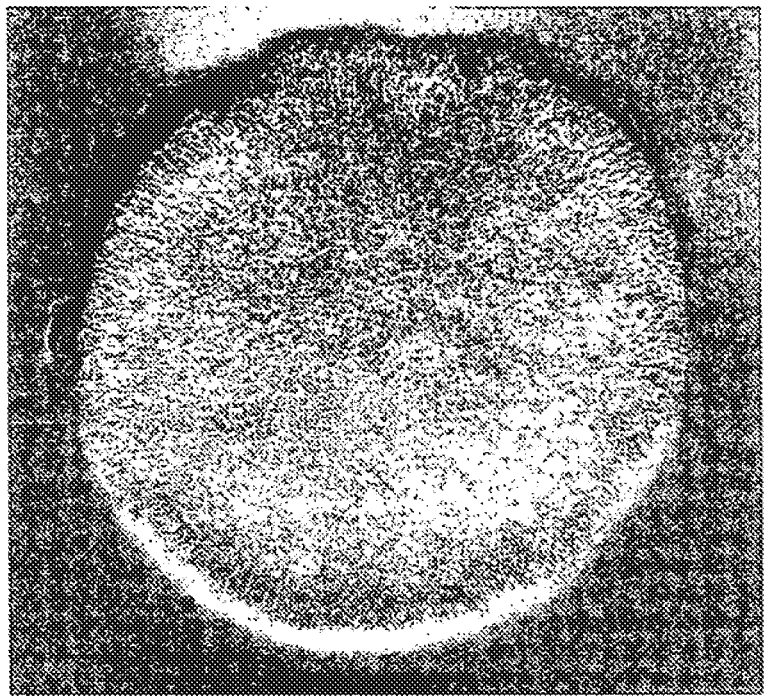
E
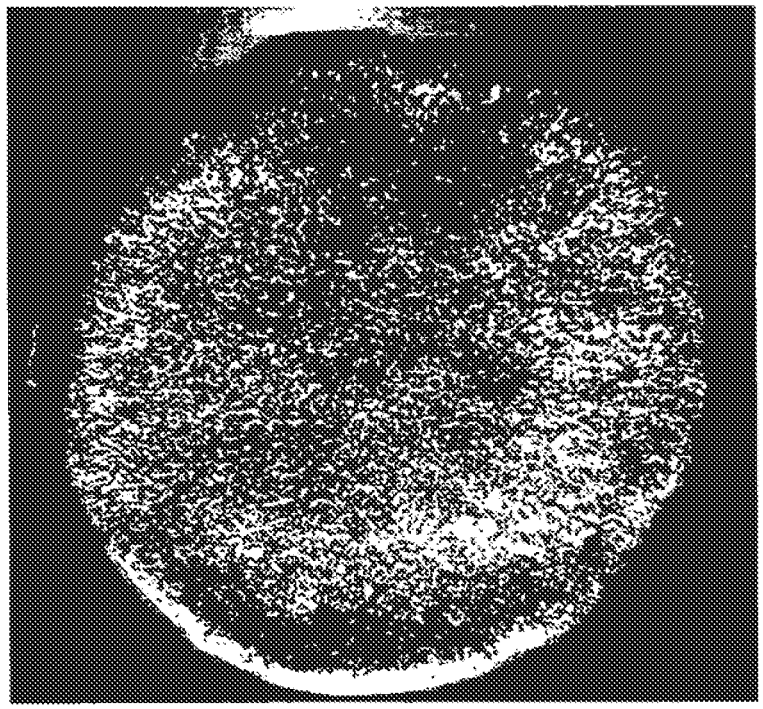
Fig. 1D-E

4mg/ml collagen, 5ml NH₃, pore size: 259±48

4mg/ml collagen, 6ml NH₃, pore size: 334±89

A

6mg/ml collagen, 2ml NH$_3$, pore size: 233±55

6mg/ml collagen, 4ml NH₃, pore size: 235±67

B

5mg/ml collagen, 1ml NH$_3$, in N$_2$ atmosphere (10 torr), pore size: 323±82

5mg/ml collagen, 3ml NH$_3$, in N$_2$ atmosphere (10 torr), pore size: 538±135

4mg/ml collagen, with surfactant (pore size: 198 ± 47) - surface

6mg/ml collagen, with surfactant (pore size: 256 ±59) - surface

8mg/ml collagen, with surfactant (pore size: 380 ±100) - surface

7A
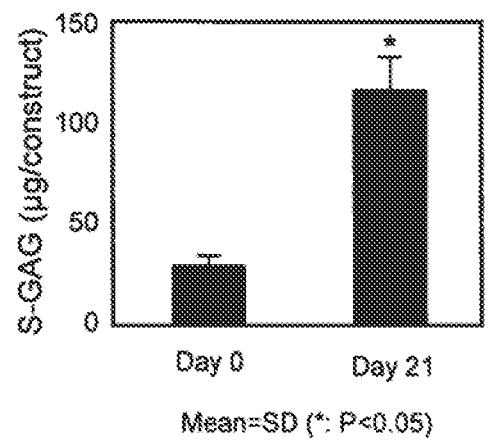
7B
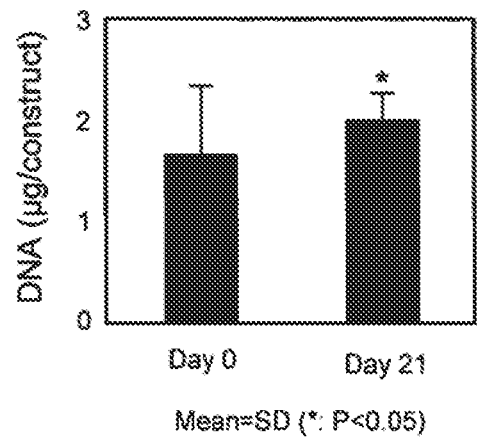
Fig. 7A-B

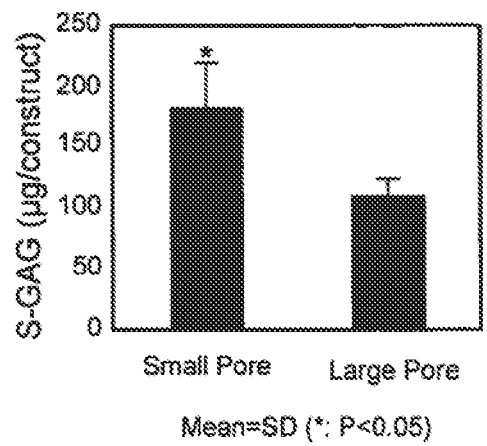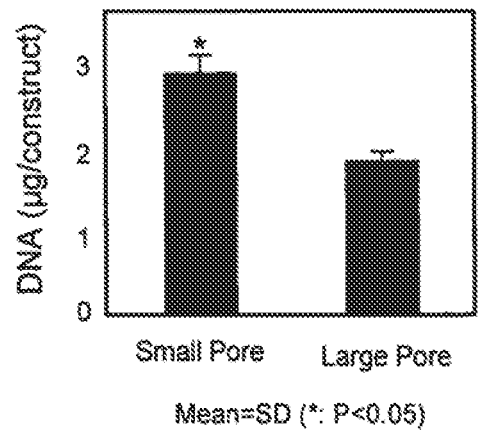
Fig. 8A-B

CELL-SUPPORT MATRIX HAVING NARROWLY DEFINED UNIFORMLY VERTICALLY AND NON-RANDOMLY ORGANIZED POROSITY AND PORE DENSITY AND A METHOD FOR PREPARATION THEREOF

CROSS-REFERENCE TO RELATED APPLICATIONS

The present application is a continuation of U.S. patent application Ser. No. 16/706,372, filed Dec. 6, 2019, which is a continuation of U.S. patent application Ser. No. 15/641,773, filed Jul. 5, 2017, which is a continuation of application Ser. No. 14/577,610, filed Dec. 19, 2014, now U.S. Pat. No. 9,701,940, which is a continuation of U.S. patent application Ser. No. 11/523,833, filed Sep. 19, 2006, now U.S. Pat. No. 8,921,109, which is based on and claims priority of the provisional application No. 60/718,714 filed on Sep. 19, 2005. The entirety of each of these applications are incorporated by reference herein.

BACKGROUND OF THE INVENTION

Field of Invention

The current invention concerns a biocompatible cell-support matrix having narrowly defined and uniformly vertically and non-randomly organized porosity and a pore density and a method for preparation thereof. In particular, the invention concerns a biocompatible cell-support matrix or support substrate having substantially the same size pores said matrix or substrate providing a support structure for live-cell suspension. The matrix has vertically non-randomly oriented open pores of substantially homogeneous pore size and narrowly defined diameter.

The support matrix seeded with the chondrocyte suspension is suitable for initiation of growth and de novo formation of hyaline or hyaline-like cartilage in vitro and in vivo as well as for preparation of cellular or acellular implants for implantation into articular cartilage in situ.

The invention additionally concerns a collagen-matrix composite system comprising of said support matrix seeded with chondrocyte suspension, said system being capable of induction of hyaline or hyaline-like cartilage from chondrocytes in vitro or in vivo when introduced into the articular cartilage in situ.

BACKGROUND AND RELATED DISCLOSURES

Collagen matrices for use as an implant for repair of cartilage defects and injuries are known in the art. Of particular interest is a honeycomb structure developed by Koken Company, Ltd., Tokyo, Japan, under the trade name Honeycomb Sponge, described in the Japanese patent JP3170693. Other patents related to the current subject disclose collagen-based substrate for tissue engineering (U.S. Pat. No. 6,790,454) collagen/polysaccharide bilayer matrix (U.S. Pat. No. 6,773,723), collagen/polysaccharide bilayer matrix (U.S. Pat. No. 6,896,904), matrix for tissue engineering formed of hyaluronic acid and hydrolyzed collagen (U.S. Pat. No. 6,737,072), method for making a porous matrix particle (U.S. Pat. No. 5,629,191) method for making porous biodegradable polymers (U.S. Pat. No. 6,673,286), process for growing tissue in a macroporous polymer scaffold (U.S. Pat. No. 6,875,442), method for preserving porosity in porous materials (U.S. Pat. No. 4,522,753), method for preparation of collagen-glycosaminoglycan composite materials (U.S. Pat. No. 4,448,718), procedures for preparing composite materials from collagen and glycosaminoglycan (U.S. Pat. No. 4,350,629) and a crosslinked collagen-mucopolysaccharide composite materials (U.S. Pat. No. 4,280,954).

However, many of the above disclosed structures have uncontrolled parameters such as uneven and uncontrolled porosity, uneven density of pores, uneven sizes of the pores and random distribution of pores within the support matrix. Such uncontrolled parameters lead to structures that are sterically unstable to provide support for cartilage matrix producing cells as these structures easily collapse upon contact with a solution or suspension containing cartilage producing cells.

There is, therefore, a need for a more uniform and sterically stable support matrix preferably prepared from a biocompatible material, such as collagen, wherein said matrix has narrowly defined size and density of pores and the pores are uniformly distributed, vertically oriented and non-randomly organized.

It is, therefore, a primary object of this invention to provide a sterically stable biocompatible, preferably collagen based matrix, having properties enabling chondrocyte attachment in numbers needed for induction and formation of hyaline or hyaline-like cartilage.

The current invention provides such matrix and/or a method for fabrication thereof by providing a sterically stable and biocompatible matrix, preferably made of Type I collagen, having narrowly defined pore sizes and density with said pores organized vertically wherein said matrix permits seeding and attachment of chondrocytes suspended in collagen, gel, sol-gel or hydrogel that gels at the body temperature, in sufficiently high numbers to induce formation of new hyaline or hyaline-like cartilage. The matrix according to the invention has a substantially narrowly defined pore size in diameter and pore density in vertically organized manner that creates an apical (top or synovial) or basal (bottom or bone) surface to the implant where the sizes and diameters of the pores on both the apical or basal surface are substantially the same. The gel system according to the invention provides conditions for a sterically-enhanced enablement of chondrocytes to produce extracellular matrix comprising glycosaminoglycan and Type II collagen and its deposition within said matrix in ratios characteristic for normal healthy articular hyaline cartilage.

All patents, patent applications and publications cited herein are hereby incorporated by reference.

SUMMARY

One aspect of the current invention is a biocompatible support matrix having narrowly defined uniformly and vertically and non-randomly organized porosity and a pore density and a method for preparation thereof.

Another aspect of the current invention is a collagen-based support matrix having narrowly defined uniformly and vertically and non-randomly organized porosity and a pore density and a method for preparation thereof.

Another aspect of the current invention is a Type I collagen-based support matrix suitable for seeding with chondrocytes suspension, said matrix having vertically oriented open pores of substantially homogeneous pore size of narrowly defined diameter of about 200±100 µm.

Still another aspect of the current invention is the support matrix suitable for growth and de novo formation of a hyaline-like cartilage in vitro and for preparation of cellular or acellular implants for in situ implantation in vivo.

Yet another aspect of the current invention is a collagen-matrix composite system comprising a Type I collagen matrix and a suspension of chondrocytes seeded into said matrix wherein said system is capable of induction of hyaline or hyaline-like cartilage from chondrocytes in vitro or in vivo when said matrix is implanted with or without cells in situ.

Another aspect of the current invention is a method for preparation of an uniform and sterically stable support matrix prepared from a biocompatible collagen material wherein said matrix has narrowly defined porosity and uniformly distributed vertically oriented and non-randomly organized pores of substantially the same size in diameter.

Still yet another aspect of the current invention is a method for preparation of a sterically stable collagen-based matrix having properties, such as a pore size of about 200±100 μm in diameter, density of about 25±10/mm$^2$ and uniform pore distribution enabling chondrocyte attachment in numbers needed for induction of formation of hyaline or hyaline-like cartilage.

Still yet another aspect of the current invention is a method for fabrication of a sterically stable type I collagen-based matrix that permits seeding of chondrocytes suspended in a Type-I collagen or in a synthetic sol-gel that gels at the body temperature wherein said matrix has a substantially narrowly defined pore size of about 200±100 μm and a pore density 25±10/mm$^2$ in a vertically organized manner that assures that pores at a top (apical) and bottom (basal) surface of the implant have substantially the same size.

Yet another aspect of the current invention is collagen, gel, sol-gel or hydrogel comprising a system that provides conditions for a sterically-enhanced induction of chondrocytes into said matrix enabling said chondrocytes to produce extracellular matrix comprising glycosaminoglycan and Type II collagen and its deposition within said matrix in the ratios characteristic for normal healthy articular hyaline cartilage.

Yet another aspect of the current invention is a method for producing a Type I collagen-based matrix for seeding chondrocytes wherein said method comprises preparation of said matrix from collagen suspension of defined collagen amount in the presence of ammonia, surfactant, at reduced pressure or in inert atmosphere or any combination of all these parameters.

Still another aspect of the current invention is a gel-matrix composite system capable of inducing cartilage production comprising a collagen-based matrix seeded with a suspension of chondrocytes in collagen or a sol-gel polymer able to gel at a body temperature.

BRIEF DESCRIPTION OF FIGURES

FIG. 1A is a schematic side view of the collagen-based matrix having a substantially homogeneous pore size of about 200±110 μm and narrowly defined porosity with chondrocytes shown as if seeded in matrix pores in a substantially same distribution pattern within the matrix.

FIG. 1B is a schematic top view of a collagen-based matrix showing a distribution of as if seeded chondrocytes within the collagen-based matrix to be substantially homogeneous within the pores having a defined diameter of about 200±100 μm.

FIG. 1D is a photograph of approximately 2.5× magnified actual Type I collagen matrix showing pore distribution within the matrix.

FIG. 1E is photograph of approximately 2.5× magnified actual Type I collagen matrix with darkened background for better contrast showing pore distribution within the matrix.

FIG. 7A is a graph showing results of determination of a content of S-GAG, measured by DMB assay, at day zero and day 21, obtained with seeding chondrocytes into the matrix having 200±50 pore sizes. FIG. 7E is a graph showing a content of DNA measured by DNA assay at day zero and day 21.

FIG. 8A is a graph showing a content of S-GAG produced by chondrocytes seeded in the support matrix having small pores (153±39 μm) or large pores (435±60 μm) FIG. 8B is a graph showing a content of DNA in the small and large pores measured by DNA assay at day zero and day 21.

DEFINITIONS

Figure 1C:
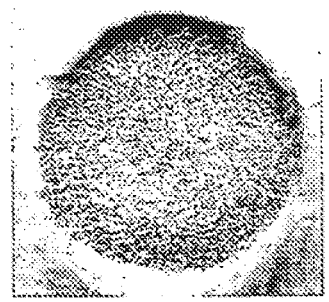
FIG. 1C is a photograph of the actual Type I collagen matrix produced according to the method of the invention without magnification.

"Sterically stable supporting structure" means nonrandom vertical orientation of collagen-fibrillar structure.

"Sterically unstable supporting structure" means random orientation mesh-like collagen-fibrillar structure.

"The matrix porosity" means a pore size defined by the diameter of holes within the support matrix or substrate as well as density of the pore distribution as a function of cross-sectional area in in millimeters.

"Substantially homogeneous" means at least 85-99% homogeneity, that is at least 85% of all pores have sizes within the given range of 200±100 μm. Preferable homogeneity is between 95 and 99%.

"Substantially homogeneous" means that a pore size and diameter is within pore size range of about 200±100 μm, preferably 200±50 μm, in diameter.

"Top surface" means an apical or synovial side of the matrix turned toward the joint.

"Bottom surface" means basal, closest to bone surface of the matrix.

"Chondrocytes" means the cells naturally residing in articular cartilage.

"About 200±100 μm" means and is intended to include also pores where the mean average is withing additional 10-20 μm on the upper side.

"S-GAG" means sulfated glycosaminoglycan.

DETAILED DESCRIPTION OF THE INVENTION

The current invention is directed to a collagen-based matrix of defined porosity having substantially homogeneous pore sizes as well as to a method for preparation thereof. The collagen-based matrix prepared according to the method of the invention has uniformly defined vertically non-randomly organized porosity and a defined pore density.

The support matrix or substrate is generally prepared from a biocompatible material such as collagen, particularly Type I collagen, and has vertically non-randomly oriented open pores of substantially homogeneous pore size of a narrowly defined diameter. The matrix is suitable for preparation of acellular implants or cellular implants seeded with chondrocytes, as well as for growth and de novo formation of hyaline or hyaline-like cartilage in vitro and in vivo.

The invention additionally concerns a collagen-matrix composite system comprising said matrix seeded with a suspension of chondrocytes in collagen, gel, sol-gel or thermoreversible hydrogel, said system being capable of enabling formation of hyaline or hyaline-like cartilage by supporting said chondrocytes in vitro or in vivo when said system is implanted into damaged or injured cartilage in situ to produce extracellular matrix and its components Type II collagen and S-GAG.

The Type I collagen-based matrix of the invention has substantially homogeneous pore size range of about 200±100 μm, preferably about 200±50 μm, in diameter. This pore size has been shown to provide the largest attachment of the chondrocytes to the pores of the matrix.

The support matrix is ultimately useful for treatment of articular cartilage injuries and lesion by providing means for growing a new hyaline or hyaline-like cartilage for treatment, replacement or regeneration of the damaged or injured articular cartilage. Such treatment is currently difficult because of the unique properties of the articular cartilage that is not the same as and does not behave as other soft tissues.

I. Articular Cartilage

Articular cartilage covers the ends of bones in synovial joints. Articular cartilage is an unique tissue in that is it is avascular, aneural and alymphatic and in mature state contains a very small number of cells. These properties are the main reason why articular cartilage has such a poor intrinsic capacity to heal (Install, J. N. and Scott, W. N., *Surgery of the Knee*, $3^{rd}$ Edition, p. 341 (2001)).

Articular cartilage is known as a relatively acellular tissue whose extracellular space is occupied by interstitial fluid (60-80%) and organic extracellular matrix (ECM) components, primarily proteoglycans and collagens.

Immature chondrocytes are the articular cartilage cells that are present in large numbers in cartilage of young individuals. The immature chondrocytes are metabolically active cells that are responsible for growth of cartilage in the young individuals. In adult individuals, where the growth of the bones has stopped, cartilage contains mature chondrocytes that are limited in number in mature quiescent cartilage and those present are mainly metabolically inactive.

The mechanical function of articular cartilage is determined by its high water content and by the particular architecture of the collagen network. This network consists of cross-linked fibrils that extend perpendicular from the subchondral bone and curve gradually to a course parallel to the articular surface in the superficial zone ("Form und Bau der Gelenkknorpel in ihren Beziehungen zur Funktion", *Z. Zellforsch.*, Vol. 2, pp. 783-862 (1925)).

Any replacement support structure should thus have orientation and organization similar to that observed naturally. Consequently, a vertical orientation of a porous structure, preferably one made of a biodegradable material used in lieu of the cartilage matrix, would seem to be an important aspect for a cartilage regeneration in vivo due to the similar structure of the native articular cartilage. Consequently, a combination of the vertical porous structure providing the necessary support combined with chondrocytes suspended in collagen, gel, sol-gel or another hydrogel would likewise seem to be beneficial for cartilage treatment in vivo or regeneration of cartilage in vitro because collagen, gel, sol-gel or another hydrogel in which the chondrocytes are suspended are biodegradable materials native or biocompatible with articular cartilage and therefore can maintain chondrocytic phenotype and stimulate cartilage extracellular matrix synthesis in vitro or in in vivo when the support matrix seeded with chondrocytes is implanted in situ.

II. Collagen-Based Matrix and a Method for Preparation Thereof

The collagen-based matrix of the invention is an essential component of a gel-matrix composite system capable of initiating the induction of hyaline-like cartilage from chondrocytes.

A. Design of the Matrix

The matrix of the invention has been designed to meet requirements of properties needed for the support matrix.

The first requirement is that the support matrix is prepared from the biocompatible and preferably biodegradable materials that are the same or similar to those observed in the articular cartilage.

The second requirement is that the support matrix has a spatial organization and orientation similar to that of the articular cartilage.

The third requirement is that the support matrix has a porosity permitting the seeding of the chondrocytes into said matrix in a number of cells that are sufficient for initiation of a formation of new hyaline or hyaline-like articular cartilage in vitro and/or in vivo.

The fourth requirement is that the support matrix has sufficient number of pores for the number of cells needed for initiation of articular cartilage formation and that the pore sizes are such that the majority of chondrocytes seeded into said support matrix are suspended within the support matrix in numbers that would result in formation of new hyaline or hyaline-like cartilage.

The fifth requirement is that the pores have substantially the same size in a range from about 200±100 μm, preferably between about 200±50 μm in pore diameter and that such size is substantially the same from the top apical to the bottom basal surface of the pores, said pores being organized vertically from the top to the bottom.

B. Support Matrix

Typically, the support matrix, preferably the collagen-based support matrix, of the invention is a three-dimensional structure made of a biocompatible and/or biodegradable material of defined density and porosity.

Typically, the support matrix is prepared from a collagenous gel or gel solution containing Type I collagen, Type II collagen, Type IV collagen, gelatin, agarose, hyaluronin, a cell-contracted collagen containing proteoglycan, glycosaminoglycan or glycoprotein, fibronectin, laminin, a bioactive peptide growth factor, cytokine, elastin, fibrin, a synthetic polymeric fiber made of a poly-acid such as polylactic, polyglycolic or polyamino acid, polycaprolactone, polyamino acid, polypeptide gel, copolymers thereof, each alone or in a combination. Additionally, the support matrix may be prepared from the collagen precursors. For example, the collagen precursors may be used to reconstitute collagen fibrillar structure for matrix protection. These precursors are, for example peptide monomers, such as alpha 1 (type I), and alpha 2 (type I) collagen peptide or alpha 1 (type I) alpha 2 (type I) peptides, in combination, or 2 (alpha 1, type I) and 1 (alpha 2, type I) peptides.

Preferably, the support matrix of the invention is prepared from collagen and most preferably from Type I collagen, containing a plurality of narrowly defined uniformly vertically and non-randomly organized pores. The pores have substantially homogeneous narrowly defined size and diameter and are uniformly distributed through the matrix dividing the matrix space into a fluid-filled column or network.

In preferred embodiments the Type I collagen-based matrix is a collagen-based sponge-like structure or honeycomb-like lattice of defined porosity having a vertically organized pores of substantially same sizes.

a. Defined Porosity

The support matrix of the invention has a certain thickness and vertically organized pores of a defined diameter oriented to create an apical (top or synovial) or basal (bottom or bone) surface of the matrix for implantation. The diameter of said pores is chosen such that the matrix in conjunction with the chondrocyte-containing gel, preferably a sol-gel, facilitates a sterically-enhanced induction of extracellular matrix glycosaminoglycan and type II collagen deposition in ratios characteristic of hyaline articular cartilage.

b. Pore Sizes

The vertically oriented cellular or acellular support matrix made of the biocompatible material having a predetermined pore size filled with chondrocytes suspension is important aspect of the quality of the repair tissue in vivo and for production of the articular cartilage in vitro.

Consequently, it is important to determine the optimal pore size for the porous matrix because the size of the pores of the matrix affects the chondrocyte attachment to the matrix walls and assures the presence of chondrocytes within the matrix needed for cartilage regeneration in vitro and in vivo. Sizes of the pores are substantially homogeneous with homogeneity above 85%, preferably 95%, most preferably about 98-99% of pores having a diameter size of about 200±100 μm, preferably 200±50 μm.

The pores of the collagen-based matrix are homogeneously distributed within said matrix to form a sponge-like structure able to taking in and evenly distributing the chondrocytes suspended in a gel solution and providing conditions conducive to producing extracellular matrix by the suspended chondrocytes.

The defined and substantially homogeneous pore size diameter of the collagen-based matrix is an important aspect of the invention. Collagen-based matrices of defined pore sizes according to the invention having different pore size diameter permit faster or slower infiltration of the chondrocytes into said matrix, faster or slower growth and propagation of the cells and, ultimately, the higher or lower density of the cells in gel-matrix system. Such pore size may be adjusted by varying the pH of the gel solution, collagen concentration, lyophilization conditions, temperature, degree of cross-linking of collagen, etc.

Generally, in the prior art structures, the pore sizes are not defined and not limited to one substantially homogeneous size. the collagen-based matrices known in the prior art are mostly structures containing pores having mixed pore sizes of from about 50 to about 2000 μm.

The support matrix of the invention has the spatial organization and orientation similar to that of the articular cartilage. The spatial organization and orientation of support matrix is schematically depicted in FIGS. 1A and 1B.

FIG. 1A is a schematic side view of the support matrix showing the vertical organization and orientation of support matrix pores seeded hypothetically with chondrocytes suspended in sol-gel.

As seen in FIG. 1A, the pores are of substantially the same size in diameter and the number of cells in each pore is also substantially the same. The cells shown here are round and touching the walls of the pores illustrating the attachment requirement for the support matrix.

Suspending solution for chondrocytes is any gel solution, preferably one containing collagen, gel, sol-gel or thermoreversible hydrogel that can change its state from sol to gel depending on the temperature.

FIG. 1B is a schematic top view, showing hypothetically the ideally homogeneous distribution of pores through the support matrix, where the pores have the same sizes and chondrocytes are evenly distributed within the pores. The pores walls that separate individual pores are also seen.

FIG. 1B is a schematic top view of a gel-matrix composite system comprising the collagen-based matrix component made of Type I collagen and embedded with chondrocytes suspended in a sol-gel showing a distribution of chondrocytes within said collagen-based matrix to be substantially homogeneous within the pores having a defined diameter of about 200 μm. The outer circle defines a size of the whole matrix wafer. Smaller circles are pores having a substantially the same size. Inside of the pore circles are chondrocytes deposited there in a sol-gel solution.

FIG. 1C is the photograph of the actual Type I collagen matrix produced according to the method of the invention without magnification. The matrix pores are visible as a black dots. The matrix can be cut to order in both directions to obtain a perfect fit, if used, for example, for an articular cartilage implant.

FIG. 1D is the photograph of 4× magnified actual Type I collagen matrix showing the pore distribution within the matrix.

FIG. 1E is photograph of approximately 4× magnified actual Type I collagen matrix with darkened background for better contrast showing the pore distribution within the matrix.

Chondrocytes suspended in a collagen, gel, sol-gel or thermoreversible hydrogel solution are introduced into narrowly defined pores of a substantially the same size and distribution within the matrix. Vertically separated columns have substantially the same diameter and defined sizes of the pores.

The pores are filled with the chondrocyte suspension. This arrangement provides sterically advantageous conditions for homogeneous distribution of chondrocyte deposition within the pores that lead to enhanced production of proteoglycans and type II collagen in ratios corresponding to the ratios observed for these compounds in the healthy hyaline cartilage.

The structural macromolecules and cartilage account for 20 to 30% of the wet weight of cartilage and includes type II collagen, large aggregating proteoglycans and non-collagenous proteins or glycoproteins. With maturation, collagen contributes over 50% and proteoglycans contribute 30-35% of the matrix dry weight.

The matrix is typically prepared as a composite cylindrical wafer seen in FIGS. 1C-1E or as a rectangular block structure cut into a wafer-like matrix construct having from about 4 mm to about 25 mm in diameter and thickness of from 0.5 to about 5 mm. The seeding density of this construct is about 25,000-300,000 chondrocytes per 25 μl of collagen solution corresponding to about 1-12 millions cells/mL. The above density numbers are exemplary only and even lesser seeding density is possible and has been shown to lead to the production of the hyaline or hyaline-like cartilage. The cell density range for seeding is preferably from about 1 to about 30 million/mL. Chondrocytes are preferably suspended in a type I or Type II collagen or in a synthetic gel, sol-gel or hydrogel and such suspension, in combination with the support matrix, forms a gel-matrix composite system of the invention.

C. Preparation of the Support Matrix

The current invention additionally concerns a novel method for preparation of the support matrix that meets the requirements stated in section IIA.

The method for preparation of the support matrix meeting such criteria involves process for standardizing the pore size, vertical orientation and organization, homogeneity and uniformity of the collagen-based matrix of the invention.

The fabrication method for preparation of the current support matrix is based on investigation of various parameters comprising the biocompatible components and/or additives and their amounts, or reaction conditions, such as, for example, pH, temperature, pressure, reduced pressure, presence of inert gasses and an apparatus for testing these parameters all alone or in various combinations.

1. Apparatus for Preparation of the Support Matrix

Fabrication set-up for preparation of the support matrix of the invention comprises variable components depending on the conditions selected for the processing.

It typically comprises a sealed container containing the biocompatible material or a precursor thereof, preferably Type I collagen, selected for the preparation of the support matrix wherein said material may be subjected to various conditions for testing and optimization or for final preparation of the support matrix. Added features may contain means for increasing or decreasing pressure, temperature, adjusting pH, adding other components, pumps, gas tanks, valves, etc.

Figure 2:
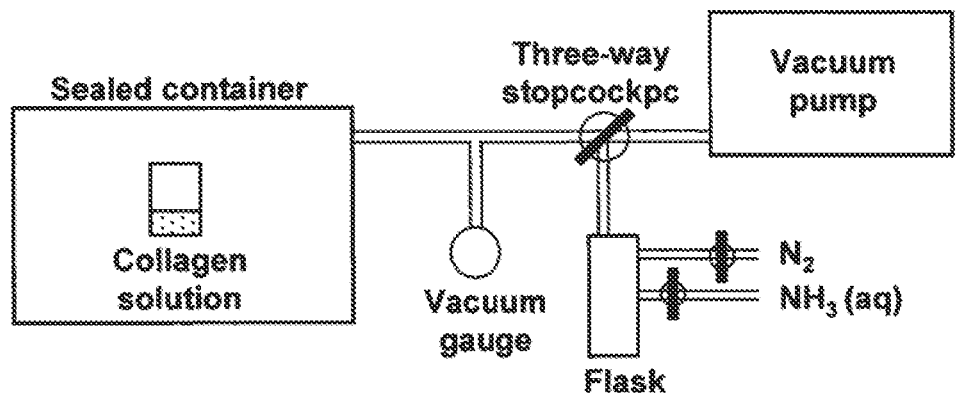
FIG. 2 is a scheme of an experimental set-up for preparation of a support matrix of the invention, providing means for storing and introduction of aqueous ammonia, introduction of inert atmosphere and creating reduced pressure.

One illustrative set-up for preparation of the support matrix is shown in FIG. 2.

FIG. 2 is schematic representation of one experimental set-up used for preparation of a support matrix of the invention, providing means for introduction of aqueous ammonia, means for reducing pressure and means for providing an inert atmosphere. Typically, the starting material, in this case the collagen solution, is placed into a sealed container having an outlet connected to a vacuum gauge that is further connected to a vacuum pump and a source of an inert gas. In FIG. 2, two sources are shown for supplying the aqueous ammonia and for storing nitrogen with a means for introducing nitrogen into the system. The starting material is then subjected to ammonia vapors by introducing a predetermined amount of aqueous ammonia into said container, and/or further introducing the inert gas, such as nitrogen or argon, or in one alternative, air, and optionally performing the reaction under reduced pressure, in the presence of a surfactant or under other reaction conditions. All these may be performed and/or tested in any combination to achieve the optimal expected results.

2. Method for Preparation of the Support Matrix

The selected criteria for the pore size of the support matrix were set to prepare the support matrix having substantially homogeneous population of pores within said matrix wherein said pores have substantially the same size in diameter of about 200±100 μm.

The preliminary studies determined that these parameters may be best met with utilizing the Type I collagen in concentrations from about 2 to about 10 mg/ml of collagen in solution, and these solutions were, therefore, further investigated for optimization of conditions for preparation of the support matrix meeting the above set criteria.

The process for optimization of conditions for preparation of the support matrix meeting these criteria involved testing of Type I collagen in 2, 4, 6, 8, and 10 mg per ml of solution, and its polymerization in the presence of 3% aqueous ammonia added in 1, 2, 3, 4, 5, and 6 ml volume. The same collagen preparations were tested with added non-ionic surfactant (Pluronic® F86, 0.3 weight/%), and the same collagen solutions were polymerized in an inert atmosphere and under reduced pressure. Various combinations of the above conditions were further tested to obtain the support matrix with the smallest and most homogeneous pore sizes.

Results are summarized in Tables 1-3 and in representative FIGS. 3-6.

a. Effect of the Ammonia Presence on Pore Sizes

In one embodiment, the support matrix was prepared from bovine Type I atelocollagen (2.9 mg/ml, pH 2.1), obtained from Inamed Corporation, Fremont, California. The collagen was concentrated by a precipitation followed by centrifugation and then dissolved in aqueous HCl in order to reach the desired concentration. The procedure for preparation of the support matrix in the presence of ammonia is described in Example 3.

The pore sizes of the support matrix obtained under these conditions are expressed as a function of collagen concentration and volume of ammonia solution/concentration, is seen in Table 1.

TABLE 1

| Collagen conc. | Volume of 3% aqueous ammonia | | | | |
|---|---|---|---|---|---|
| | 2 ml | 3 ml | 4 ml | 5 ml | 6 ml |
| 2.8-2.9 mg/ml | — | — | No pores | — | No Pores |
| 4 mg/ml | — | 256 ± 68 | 274 ± 87 | 259 ± 48* | 334 ± 89 |
| 6 mg/ml | 233 ± 55 | 365 ± 107 | 235 ± 67* | — | — |

TABLE 1-continued

| Collagen conc. | Volume of 3% aqueous ammonia | | | | |
|---|---|---|---|---|---|
| | 2 ml | 3 ml | 4 ml | 5 ml | 6 ml |
| 8 mg/ml | 284 ± 90* | 299 ± 73 | 1195 ± 294 | — | — |
| 10 mg/ml | 474 ± 108* | — | Few pores | — | — |

Pore size was measured within 1 mm of the surface of the formed matrix.

As seen in the Table 1, polymerization of collagen solution containing between 2.8 and 2.9 mg/ml did not result in a porous matrix formation regardless how much ammonia was added. Collagen at 4 mg/ml and at 3 ml or 5 ml ammonia polymerized into the matrix having a preferred and/or acceptable pore sizes in the range of 256±68 μm and 259±48 μm, respectively. At 6 ml of ammonia, the matrix formed with pore sizes in the range of 334±89 μm.

Figure 3A:
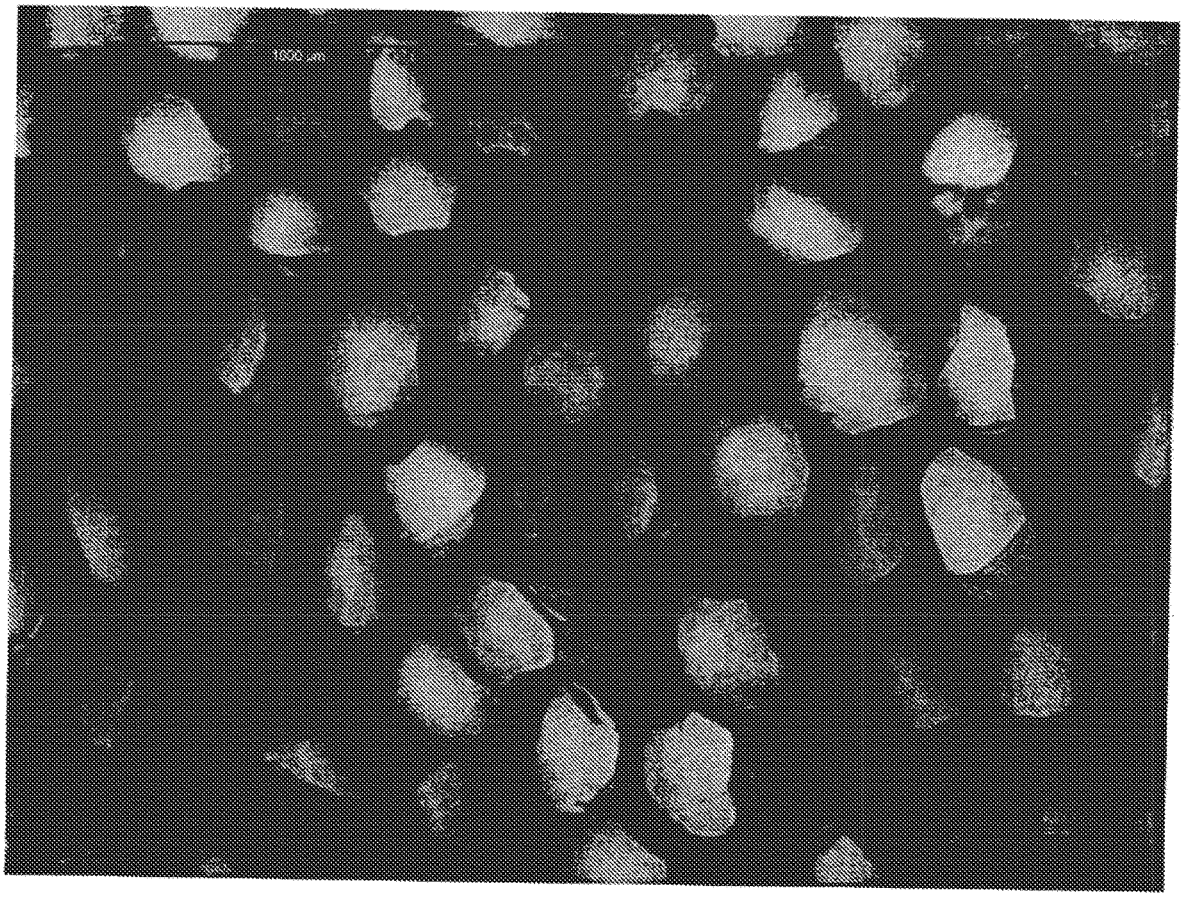
FIG. 3A is a microphotograph of a Type I collagen-based matrix prepared from 4 mg/ml of collagen in the presence of 5 ml of 3% ammonia, showing the pore size about 259±484 μm. The FIG. 3A clearly shows that the matrix has pores of substantially the same size and an equal distribution throughout the matrix. When the ammonia volume was increased to 6 ml, the pore size increased to 334±891 μm, as seen in FIG. 3B. Scale (1000 μm, i. e. 1 cm) is shown in upper left corner.
Figure 3B:
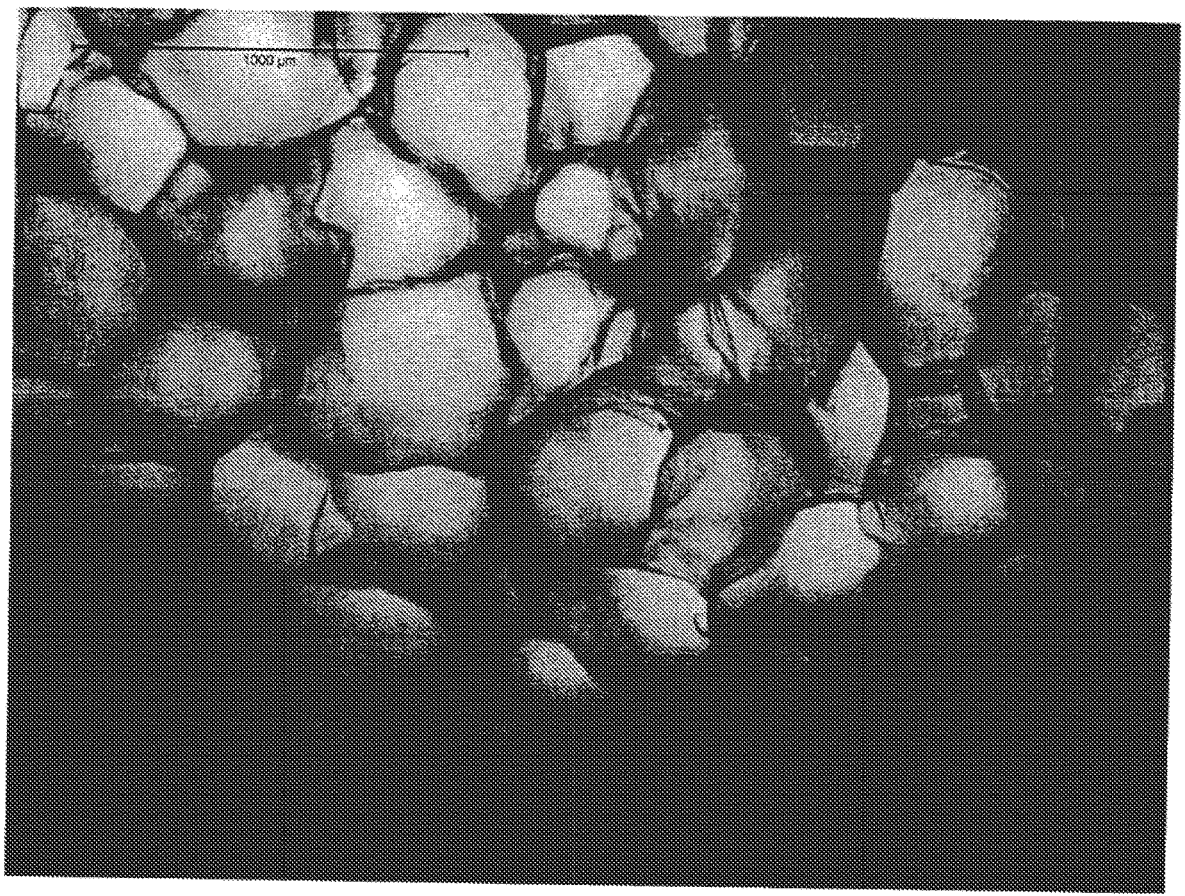

FIG. 3A and FIG. 3B are representative microphotographs of support matrices prepared from 4 mg/ml collagen in the presence of 5 or 6 ml of ammonia resulting in pore sizes ranges of about 259±48 μm and about 334±89 μm, respectively. Both microphotographs are on the same scale (scale 1000 μm) and the difference in their sizes is clearly visible.

Collagen in concentration of 6 mg/ml polymerized in the presence of 2 ml or 4 ml ammonia yielded the support matrix having pore sizes in the optimal range of about 233±55 μm and about 235±67 μm, respectively. At 6 ml of ammonia, the matrix formed with pore sizes in the range of 334±89 μm.

Figure 4A:
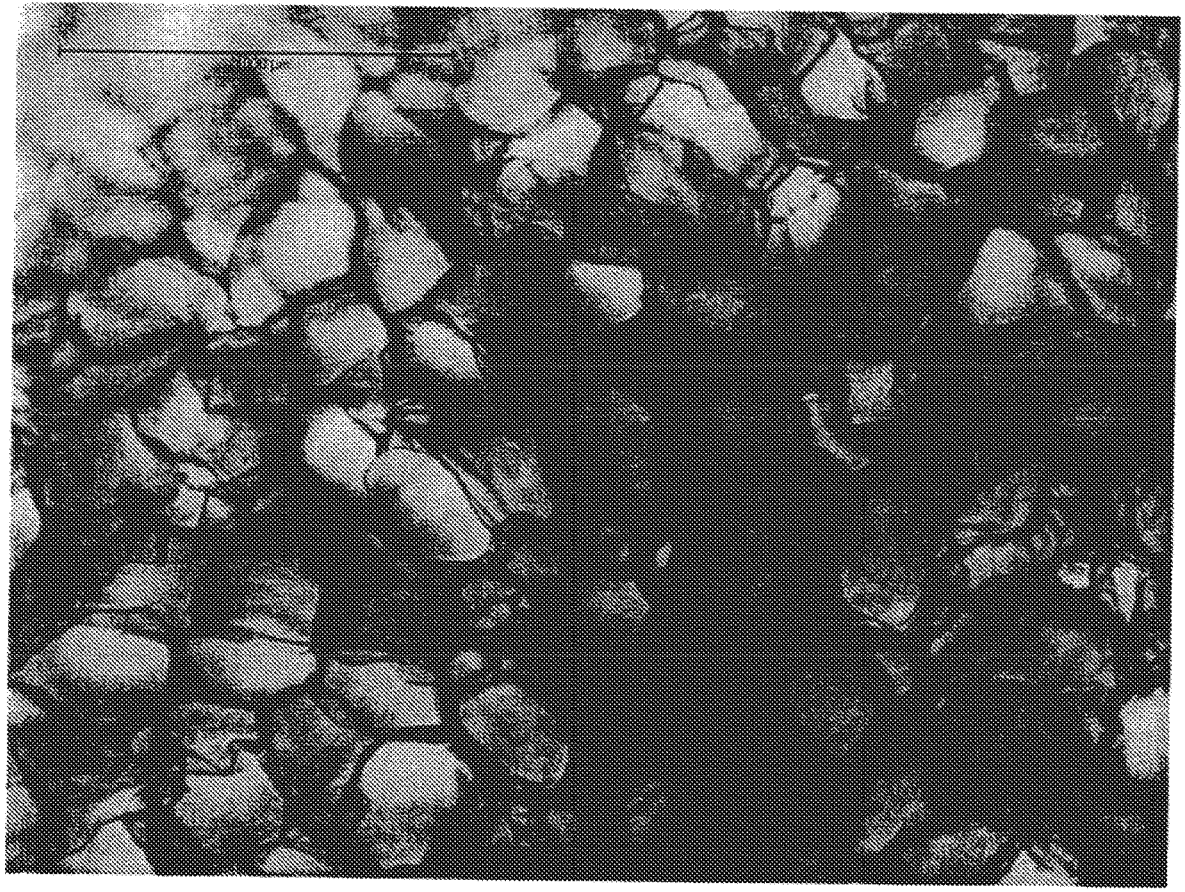
FIG. 4A is a microphotograph of a Type I collagen-based matrix prepared from 6 mg/ml of collagen in the presence of 2 ml of 3% ammonia, showing the pore size 233±55 μm, where the pore size and distribution of pores through the matrix is substantially the same. When under the same conditions, the ammonia volume was increased to 4 ml, the pore size increased only slightly to 235±67 μm, as seen in FIG. 4B. Scale (1000 μm, i. e. 1 cm) is shown in upper left corner.
Figure 4B:
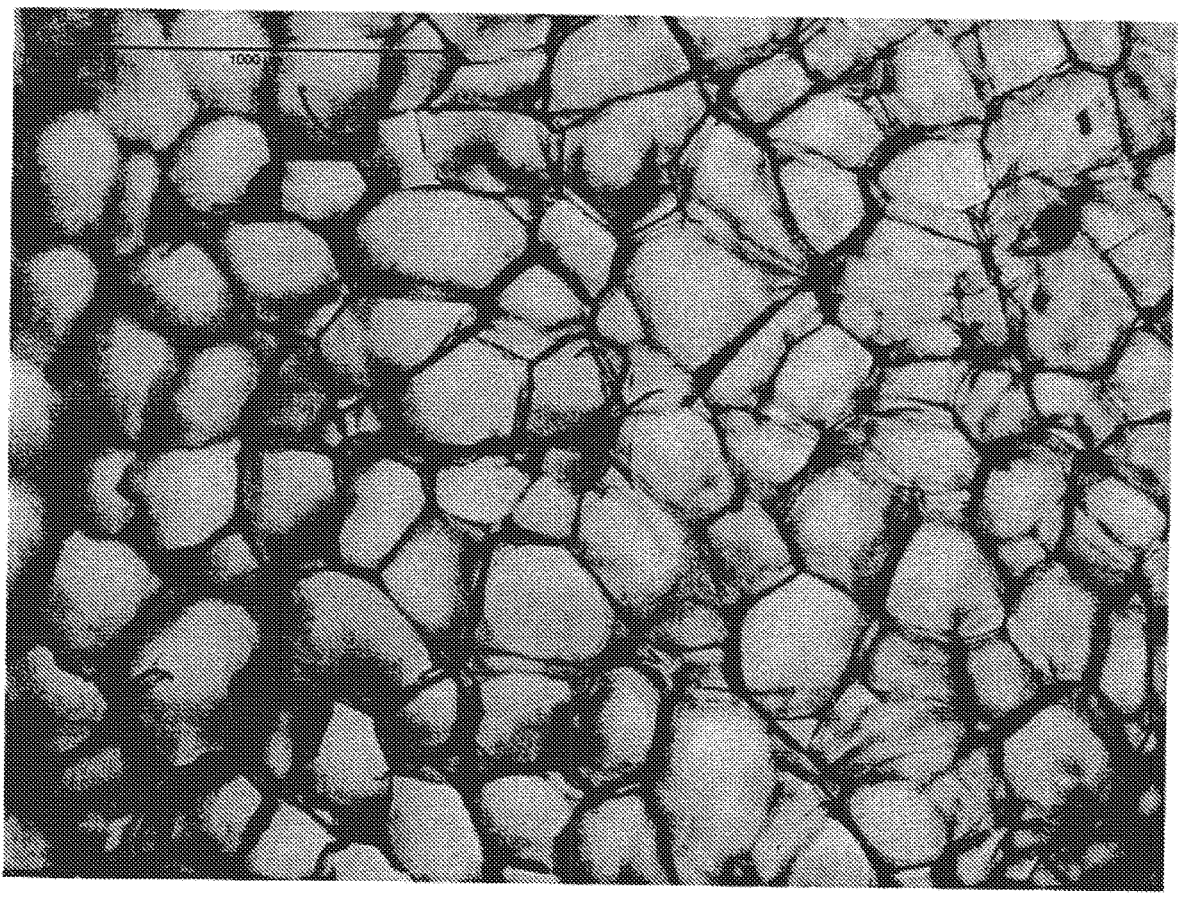

FIG. 4A and FIG. 4B are representative microphotographs of support matrices prepared from 6 mg/mi collagen and 2 or 4 ml of ammonia resulting in pore sizes ranges of about 233±55 μm and about 235±67 μm. Both microphotographs are on the same scale (scale 1000 μm). Both microphotographs show the pores to be of approximately the same size. Homogeneity of their distribution is clearly visible.

Polymerization of collagen at 8 mg/ml collagen and at 2, 3, and 4 ml of ammonia resulted in the support matrix having larger pores in ranges 284±90 μm, 299±73 μm and 1195±294 μm, respectively. At 10 mg/ml polymerization yielded a matrix with pores in the range of 474±108 μm exemplifying inherent variability occurring with higher concentrations of collagen.

As seen from these results, the support matrix prepared with a moderate amount of collagen between 4 and preferably 6 mg/ml, in the presence of moderate volume of ammonia, between 2 and 4 ml resulted in the matrix having the pore sizes within the optimal range of about 200±100 μm.

b. Effect of the Inert Atmosphere and Reduced Pressure

In another embodiment, the support matrix was prepared from bovine Type I atelocollagen, as already described above and the support matrix was prepared in the inert nitrogen atmosphere and at reduced pressure. The procedure conditions for preparation of the support matrix in the presence of ammonia and at inert atmosphere and reduced pressure is described in Example 5.

The support matrix obtained under these conditions and the pore sizes expressed as a function of collagen concentration and volume of ammonia solution/concentration are seen in Table Table 2

TABLE 2

| Volume 3%/NH3 | Final pressure | Pore size (μm) |
|---|---|---|
| 1 ml | 10 torr | 323 ± 82* |
| 1 ml | 3 torr | 253 ± 59* |
| 3 ml | 10 torr | 538 ± 135 |
| 6 ml | 3 torr | 557 ± 148 |

Table 2 shows the pore size as a function of volume of ammonia solution/concentration and reduced pressure. Pore size is measured within 1 mm of the surface of the formed scaffold.

As seen at Table 2, at a collagen concentration of 5 mg/ml in all instances, and with presence of 1, 2 or 3 ml ammonia, the smallest pores were obtained in an inert atmosphere combined with reduced pressure at three torr. In that instance, the pore sizes were in the range from 253±59 μm. All other combinations resulted in larger pore sizes above 300 μm.

Figure 5A:
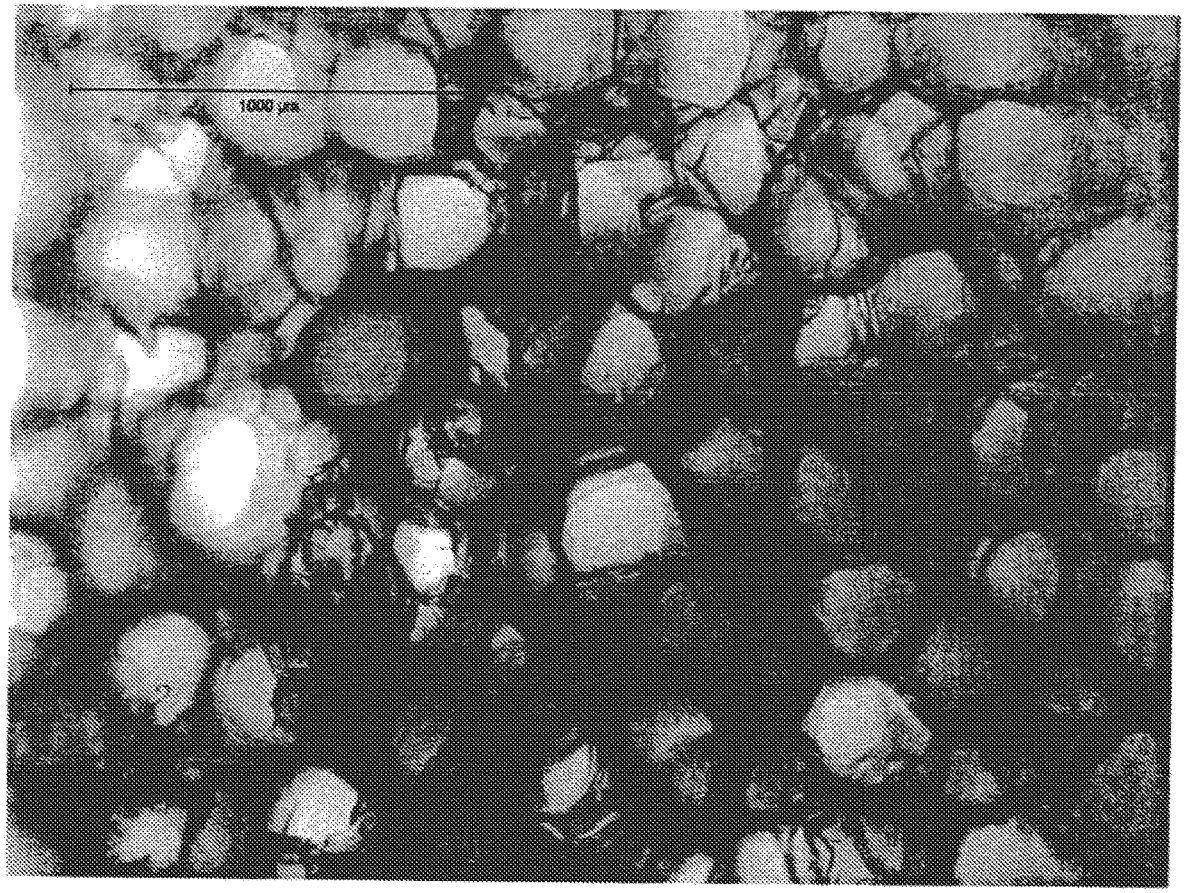
FIG. 5A is a microphotograph of a Type I collagen-based matrix prepared from 5 mg/ml of collagen in the presence of 1 ml of 3% ammonia prepared in an inert (nitrogen) atmosphere under reduced pressure (3 torr), showing the pore size 253±59 μm, wherein the pore size and distribution of pores through the matrix are substantially the same. When under the same conditions, the nitrogen atmosphere pressure was further decreased to 10 torr, the pore size increased to 323±82 μm, as seen in FIG. 5B. When under the same conditions the ammonia volume was increased to 3 ml, the size of pores increased to 538±135 μm, as seen in Figure SC. Scale (1000 μm, i. e. 1 cm) is shown in upper left corner.

FIG. 5A shows the pore size of 253±59 μm of the matrix made of the polymerization of 5 mg/ml collagen with 1 ml of ammonia in nitrogen atmosphere at reduced pressure to three torr.

Figure 5B:
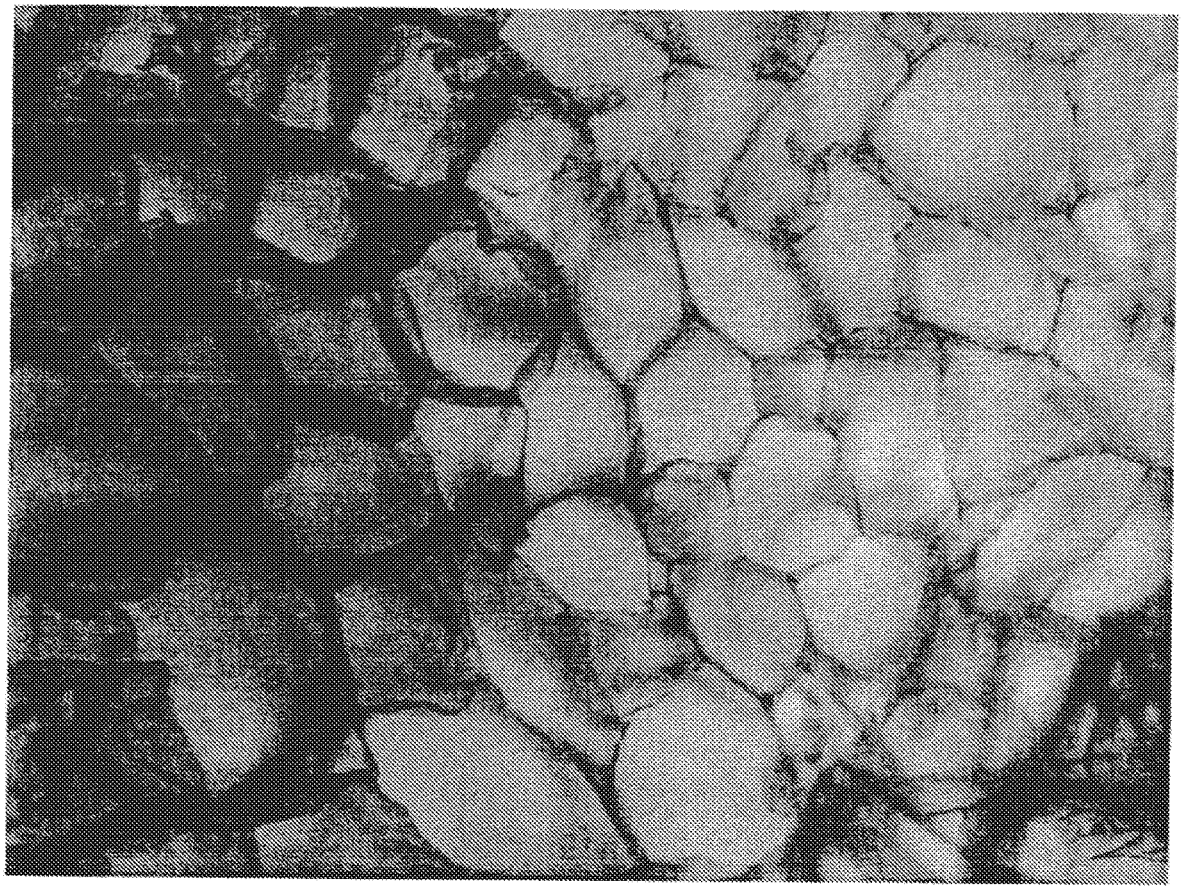
Figure 5C:
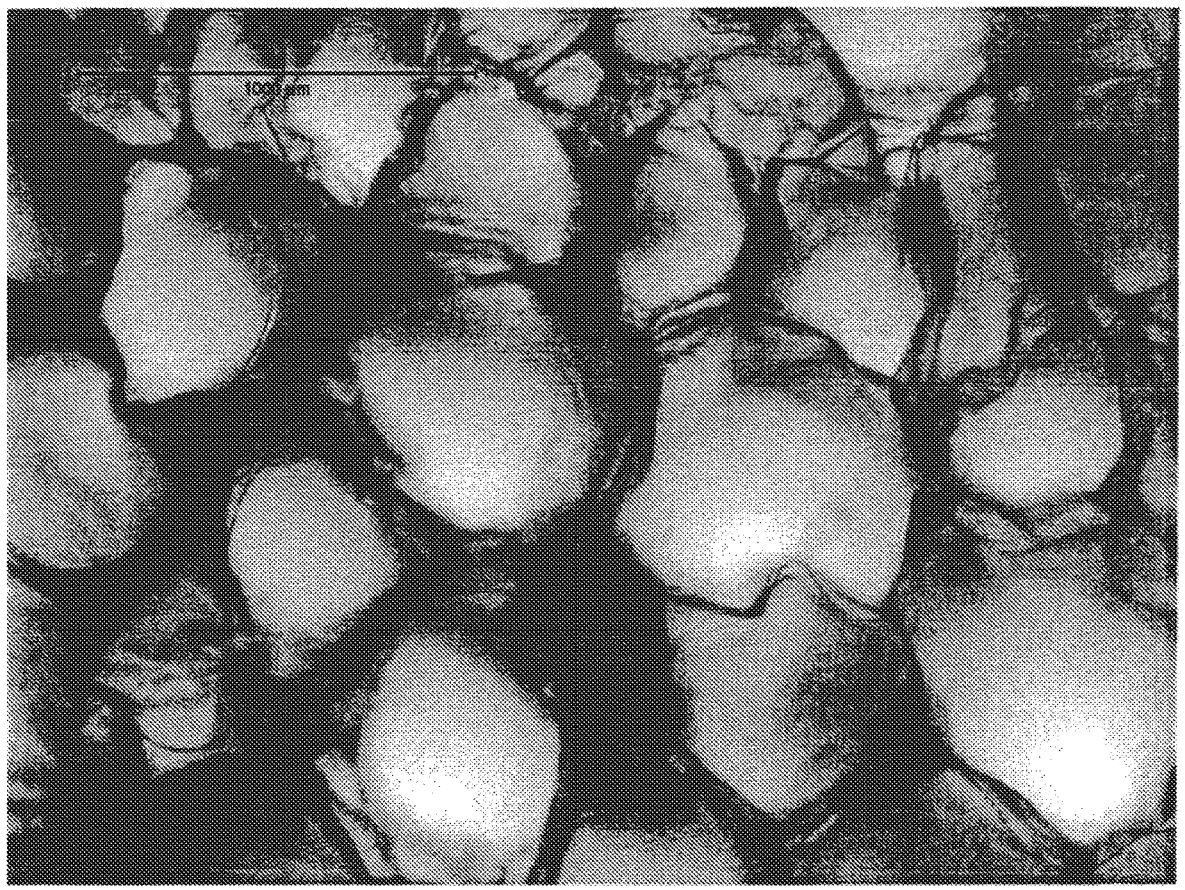

FIG. 5B shows the matrix having a pore size of 323±82 μm made of the polymerization of 5 mg/ml collagen with 1 ml of ammonia in nitrogen atmosphere at reduced pressure to 10 torr, FIG. 5C shows the pore size of 538±135 μm of the matrix made by polymerization of 5 mg/ml collagen with 3 ml of ammonia in nitrogen atmosphere at reduced pressure to 10 torr.

As seen from these results, the support matrix prepared with a small volume of ammonia combined with a moderate reduction of pressure performed in an inert atmosphere resulted in the matrix having the pore sizes within the optimal range of about 200±10 μm.

c. Effect of a Surfactant on Pore Sizes

In another embodiment, the support matrix was prepared from bovine Type I atelocollagen, as described above. The procedure for preparation of the support matrix in the presence of surfactant is described in Example 4.

The support matrix obtained under these conditions and the pore size is expressed as a function of collagen concentration in the presence of the 0.3% by weight of Pluronic® surfactant is seen in Table 3.

TABLE 3

| Collagen Conc. | Pore size (μm) |
|---|---|
| 4 mg/ml | 198 ± 47* |
| 6 mg/ml | 256 ± 59* |
| 8 mg/ml | 380 ± 100* |

Pore size seen in Table 3 is expressed as a function of collagen concentration. Pore size is measured within 1 mm of the surface of the formed matrix.

As seen in Table 3, at a concentration of collagen at 4 mg/ml and in the presence of the surfactant, the pore size of the support matrix was about 198±47 μm. At 6 mg/ml and at 8 mg/ml of collagen, the support matrix had pore sizes in the range from about 256±59 μm and about 380±100 μm.

Figure 6A:
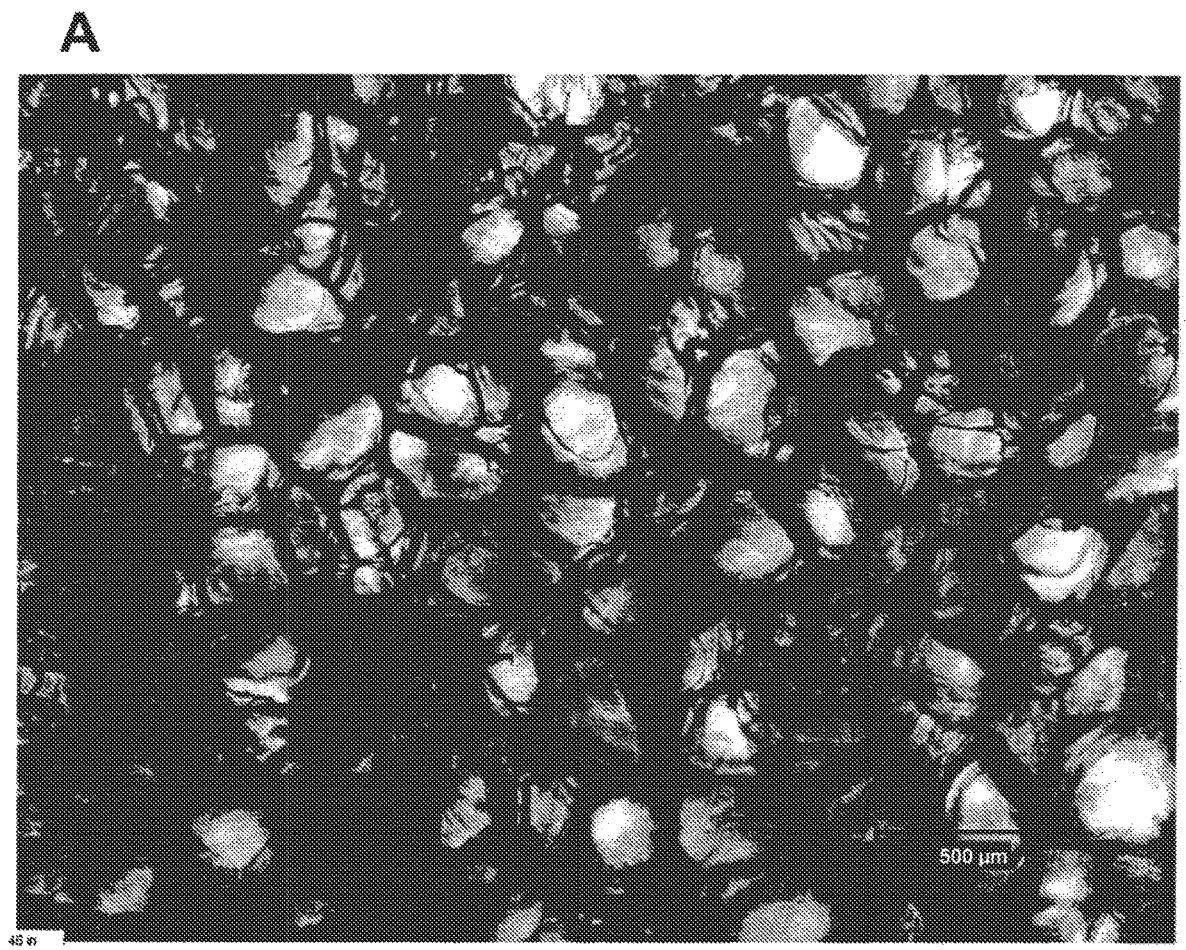
FIG. 6A is a microphotograph of a Type I collagen-based matrix prepared from 4 mg/ml of collagen in the presence of 5 ml of 3% ammonia prepared in the presence of non-ionic surfactant (Pluronic® F68; 0.3% weight/%). The pore size at the surface of the matrix was 198±47 μm, showing the pore size and distribution of pores through the matrix to be homogeneous and the pore sizes substantially the same. When under the same conditions, the amount of collagen was increased to 6 mg/ml, the pore size increased to 256±59 μm, as seen in FIG. 6B. When under the same conditions the collagen was increased to 8 mg/ml, the size of pores rose to 380±100 μm, as seen in FIG. 6C. Scale is 500 μm shown in lower right corner.
Figure 6B:
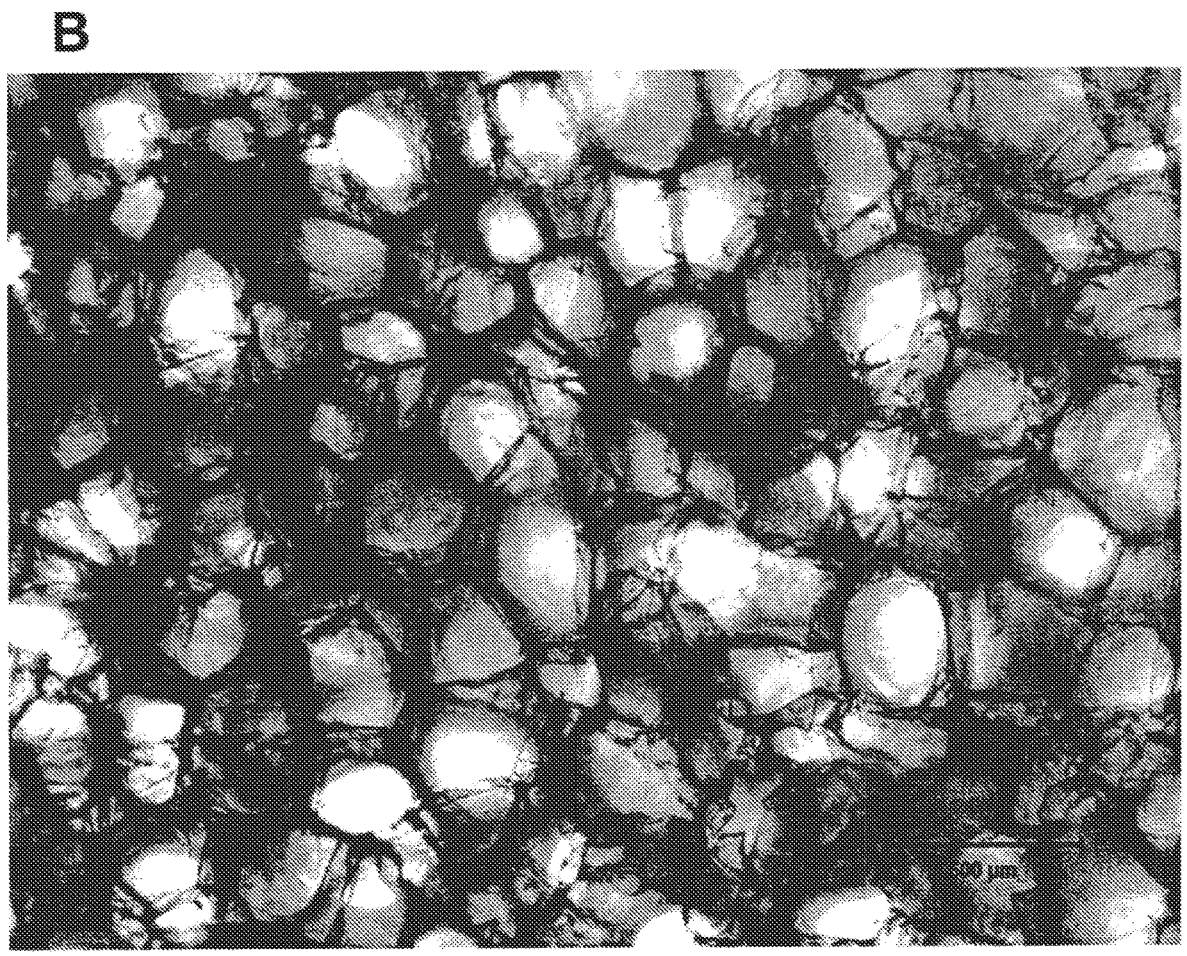
Figure 6C:
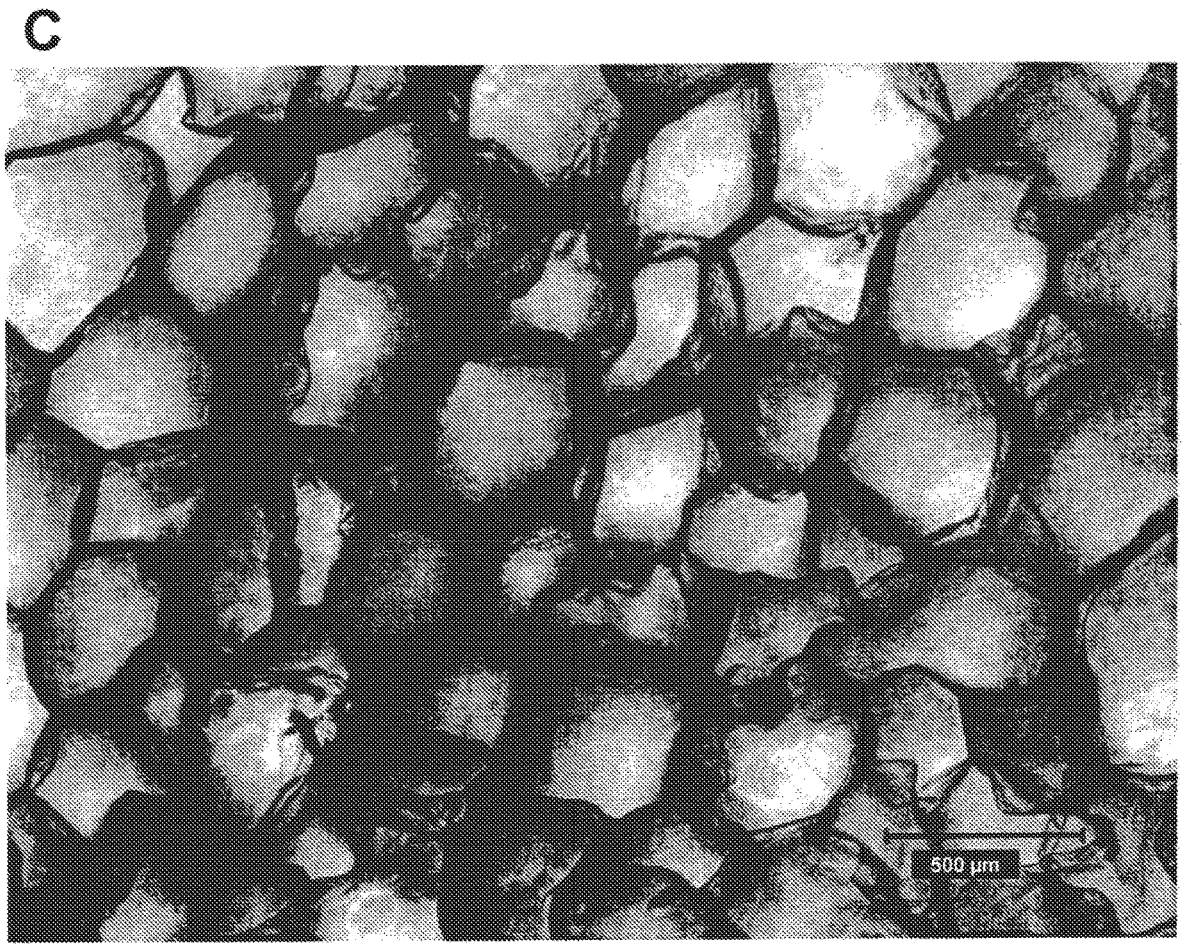

FIGS. 6A, 6B and 6C, having the same scale, are the microphotographs of matrices resulting from polymerization of 4, 6 and 8 mg/ml of collagen in the presence of the surfactant. These figures again clearly show the uniformity and homogeneity of the resulting pores as well as their uniform sizes.

Presence of the surfactant in the collagen pre-polymerization mixture clearly affects the formation of pore sizes within the optimal ranges, particularly when combined with lower concentration of collagen, polymerization of collagen (4 mg/ml) resulted in matrix having optimally sized pores of about 198±47 μm.

d. Other Factors

Some other factors may also positively affect the pore sizes similarly to the above described ones.

For example, the collagen precursors may be used to reconstitute collagen fibrillar structure for matrix protection. These precursors are, for example peptide monomers, such as alpha 1 (type I), and alpha 2 (type I) collagen peptides or in combination of 2 (alpha 1, type I) and 1 (alpha 2, type I) peptides, or 3 (alpha I, type II) peptides.

The other factors that may be manipulated are the selective vortical shearing of the peptide monomer, the chemical composition and pH of the solubilization buffer.

The vortical shearing step determines the dispersion and alignment of the associated collagen fibrils of alpha I (type I) and alpha II (type I) peptides. During this procedure equilibration in a nitrogen or argon atmosphere controls pH.

Other factors that may be used are the neutralization reactants for polymerization, temperature, rate and percentage of water removal.

Exemplary conditions for preparation of the collagen-based matrix are as follows.

The concentration of Type I collagen for fabrication of the collagen-based matrix is about from about 2 to about 10, preferably from about 4 to about 8, most preferably about 4 to about 6 mg/ml. Such concentration of collagen is critical for the initial polymerization resulting in fibrillogenesis, that is for formation of fibrils. Prior and current studies show that at the concentration of collagen below 3 mg/ml there is no fibrillogenesis, and thus no pore formation, unless such is promoted by addition of some other components.

The suitable buffers for solubilization of the Type I collagen are, for example, a formic acid containing buffer at pH 4.8, acetic acid containing buffer at pH 5.0 or a diluted hydrochloric acid at pH 3.0.

The shearing of the collagen solution is set, for example, to be for about 10-60 seconds at 10-100 dynes/cm$^2$.

The sheared peptides are equilibrated in an inert gas atmosphere such as nitrogen or argon gas for about 30 minutes to about 2 hours at about 4° C. The use of the inert gas displaces air containing oxygen that may act as an oxidant and decrease fibrillogenesis. This factor was found to positively affect the polymerization and pore formation.

Neutralization is typically carried out in a vapor of about 0.3% ammonia over about 12 to about 24 hour period. This factor has also been found to affect the collagen polymerization and formation of pores having homogeneous pore size.

Freezing, if there is, is carried out at −40° C. to about −60° C. over a period of about 2 to about 12 hours.

Water removal is achieved by exposure to an anhydrous atmosphere from −20° C. to about 50° C. preferably at 37° C. for about 24 to about 48 hours.

The gradual nature of the polymerization and slow process of water removal typically maintains the architectural elements of the scaffold collagen-based to achieve the proper orientation and diameter of the longitudinal pore structure necessary for hyaline cartilage extracellular matrix deposition by the cells.

The organization of the newly synthesized cartilage specific matrix within the porous type I collagen is visualized and quantified by, for example, ELISA/Western blot methods for determination of protein levels or quantitative RT-PCR or real-time PCR for m-RNA level.

III. Sterically-Enhanced Induction of Hyaline Cartilage

A main aspect of the current invention is a finding that when the pore sizes are substantially homogeneously restricted to a narrowly defined diameter, preferably to a pore size diameter of about 200±100, preferably 200±50 μm, and when such pores are vertically organized, such diameter of said pores in conjunction with the chondrocyte suspension facilitates a sterically-enhanced enablement of hyaline cartilage leading to formation of extracellular matrix. Such sterically-enhanced enablement leads to a deposition of collagen Type II and proteoglycans within the matrix in ratios characteristic of articular cartilage.

IV. Gel-Matrix Composite System Capable of Inducing Cartilage Production

In one embodiment, the invention concerns a collagen-based matrix prepared from Type I collagen seeded with chondrocytes suspended in synthetic sol-gel, which gels at body temperature. The gel-matrix composite system comprises a matrix having pore diameters of about 200±100 μm, preferably 200±50 μm, that permit uniform infusion of chondrocyte/gel suspensions into the pores, and induces deposition of collagen Type II and proteoglycans (glycosaminoglycans) within the matrix in ratios characteristic of articular cartilage.

The collagen-based matrix of the current invention acts like a porous sponge when infiltrated with the suspended chondrocytes by, for example, wicking or infusion, wherein the cells are distributed within the matrix pores.

This arrangement permits chondrocytes to migrate and settle in the support matrix in a sterically-enhanced fashion and enables them to proliferate and secrete materials for generation of new extracellular matrix and eventually producing a hyaline cartilage.

Suspending solution for chondrocytes is any gel solution, preferably one containing collagen, gel, sol-gel or thermoreversible hydrogel that can change its state from sol to gel depending on the temperature, and is preferably a thermoreversible gelation hydrogel (TRGH) material in which the sol-gel transition occurs on the opposite temperature cycle of agar and gelatin gels. Consequently, the viscous fluidic phase is in a sol stage and the solid phase is in a gel stage. TRGH has very quick sol-gel transformation which requires no cure time and occurs simply as a function of temperature without hysteresis. The sol-gel transition temperature for embedding chondrocytes within the collagen-based matrix is set at a temperature where the sol-gel is in a sol state whereas the temperature for stabilizing the chondrocytes within the matrix is set at a body temperature in the range of about 37° C.

V. Comparative Experimental Studies

Comparative experimental studies were performed in order to biochemically evaluate a porous matrix seeded with a chondrocyte suspension in collagen and to further evaluate the effect of pore size of the porous support matrix on the chondrocytes proliferation and extracellular matrix formation.

These studies were performed using human chondrocytes. Healthy human articular cartilage (hAC) tissue was obtained from the Tissue Bank, The National Disease Research Interchange, Philadelphia, PA. The cartilage tissue was digested, isolated chondrocytes were seeded on culture dishes and precultured for monolayer cell expansion. Isolated chondrocytes were seeded in a 3D culture, according to a procedure described in Examples 7 and 8.

A. Cell Seeding and Time-Dependent Production of Proteoglycan

For this study, the production of total sulfated glycosaminoglycan (S-GAG) content was measured by DMB assay after 0 and 21 days of culture.

The experimental set-up is described in Example 6. Briefly, the cells were seeded into the support matrix and cultured over night and their S-GAG content and DNA (showing a number of cells) was determined at days zero and 21.

Results are summarized in Table 4 and FIGS. 7A and 7B.

TABLE 4

Results of Biochemical Evaluation

| Biochemical | Day 0 | | Day 21 | |
|---|---|---|---|---|
| Results | Mean | SD | Mean | SD |
| S-GAG accumulation | 28.53 | ±4.35 | 117.42* | ±16.55 |
| DNA contents | 1.69 | ±0.66 | 1.98 | ±0.30 |

*P < 0.05

At day 0, the average of S-GAG content was 28.53±4.35 μg. At day 21, the amount of S-GAG was 117.42±16.55 μg (Table 4 and FIG. 7A). The S-GAG accumulation in the matrix at day 21 was significantly increased as compared to that at day 0. Results are seen in Table 4 and in FIG. 7A.

At day 21, the S-GAG accumulation was 4.2 fold greater than that at day 0 ($P < 0.01$). No statistical difference of the DNA content between day 0 and 21 was observed, however tendency of increasing DNA content was observed at day 21 as compared to day 0.

FIG. 7A shows results of the DB assay where the S-GAG content was determined on day zero and day 21. As seen in FIG. 7A, culturing of the composite for 21 days led to a substantially increased production of S-GAG. In contrast, the production of DNA did not increase under these conditions, as seen in FIG. 7B, where DNA in μg/composite was determined.

In the novel composite of collagen-based porous matrix comprising chondrocytes suspended in a collagen hydrogel, chondrocyte proliferation and enhanced cartilage accumulation was observed. This finding indicates that the composite of the collagen-based porous matrix and hydrogel suspension of chondrocytes is beneficial for cell adherence and proliferation and accumulation of the cartilage specific Extracellular Matrix in vitro.

B. Evaluation of the Effect of Pore Size of the Collagen-Based Support on Extracellular Matrix Production For the evaluation of the effects of the pore size on biochemical parameters, the total S-GAG content was measured by DMB assay after 21 days of culture. Experimental procedure is described in Example 8.

The average of S-GAG content in constructs with a small pore size was 183.01±39.78 μg (Table 5 and FIG. 8A). AS seen in Table 5 in Figure BA, the amount of S-GAG in constructs with a large pore size was 115.56±13.50 μg (Table 4 and FIG. 8A). The S-GAG accumulation in constructs with small pore size was significantly greater than that with large pore size (Table 5 and FIG. 8A).

The S-GAG accumulation in constructs with small pare size was 1.6-fold greater than that with large pore size (Table 5 and FIG. 8A) (P<0.05).

The DNA content in constructs with a small pore size was significantly greater than for constructs with a large pore size (Table 5 and FIG. 8A). The DNA content in constructs with a small pore size was 1.5-fold greater than that with a large pore size (Table 5 and FIG. 8A) (P<0.05).

TABLE 5

Results of Biochemical Evaluation

| Biochemical | Small Pore | | Large Pore | |
|---|---|---|---|---|
| Results | Mean | SD | Mean | SD |
| S-GAG accumulation | 183.01* | ±39.78 | 115.56 | ±13.50 |
| DNA Contents | 2.78* | ±0.21 | 1.81 | ±0.10 |

*P < 0.05

Results of this study are illustrated in FIGS. 8A and 8B. FIG. 8A shows results obtained in DMB assay where the S-GAG content per/composite is shown for a composite having large or small pores. As seen in FIG. 8A, small pores composites produced approximately one halt more of S-GAG than the composite having large pores. Similar results were seen in FIG. 8B illustrating a DNA content in composite having a large or small pores. As observed for S-GAG. The DNA content in the composite having smaller pores was significantly higher then in the composite having a large pores.

As clearly seen in FIG. 8A, the production of S-GAG provides evidence that the cartilage ECM formation was significantly higher in composites having the small pores when compared to composites having the large pores. FIG. 8B is a graph showing a content of DNA, measured by DNA assay, in composites having small pores (153±39 μm) or large pores (435±60 μm). As clearly seen in FIG. 8B, the production of DNA was significantly higher in the composites having smaller pores as compared to that with larger pores.

Small pore size of the composite porous matrix shows significant cell proliferation and cartilage specific accumulation in the matrix as compared to that of large pore size.

C. Viability Determination

To establish biocompatibility of the support matrix of the invention, viability studies were performed. Experimental procedure is described in Example 9.

The matrices prepared with different collagen concentrations in the presence of surfactant readily absorbed the chondrocyte-laden gel. As seen in Table 6 below, the cell counts were consistent with the pore size distribution present in FIG. 6, with a cell viability of 98-99%.

TABLE 6

| Group | Mean cell count ±SD | Mean % Viability | Comments |
|---|---|---|---|
| Table 6: 4 mg/ml collagen with Pluronic | 100,800 ± 41,692 | 98.7 | |
| Table 6: 6 mg/ml collagen with Pluronic | 103,500 ± 15,679 | 99% | |
| Table 6: 8 mg/ml collagen with Pluronic | 88,350 ± 2,758 | 99.0 | |

VI. Method for Use of Gel-Matrix Composite System

The matrix and a system of the invention are useful for production of hyaline cartilage in situ or in vitro. In both cases, the collagen-based matrix is prepared as a matrix wafer. For in situ use that is achieved by way of an implant, the matrix wafer is cut into a size of the cartilage defect and introduced into the cartilage defect or lesion or the cartilage with some bone loss such as osteochondral defects.

The chondrocytes suspension is then introduced as a sol under colder than body temperature into said matrix emplaced in the lesion or defect thereby generating a gel-matrix composite system in situ and the temperature is raised to the body temperature whereby the sol is transitionally changed into a gel.

In alternative, the invention works in the same way for acellular implant where the collagen-based matrix filled with the sol-gel is introduced without chondrocytes. The implant is left in the body until the new hyaline cartilage is generated and the matrix which is biodegradable self-degrades.

For in vitro use, the process is similar but proceeds in the tube or Petri dish under the same conditions until the hyaline cartilage is produced. Such cartilage may then be used as an implant into the cartilage defect or lesion.

Example 1

Preparation of the Collagen-Based Matrix

This example describes one exemplary method for preparation of the collagen-based matrix.

Type I collagen is dissolved in a formic acid buffer at pH 4.8 and its concentration is adjusted to about 5.2 mg/ml. The solution is subjected to a vortical shearing for 10 seconds at 10 dynes per cm. The sheared peptides is then equilibrated in nitrogen gas for 30 minutes at 4° C. to displace air. Neutralization is carried out in a vapor of 0.3% ammonia over a 24 hour period. The solution is then subjected to freezing at −40° C. over a period of 2 hours. Water is removed by exposing the frozen solution to an anhydrous atmosphere at 37° C. for 24 hours.

The organization of the newly synthesized cartilage specific matrix within the porous type I collagen is visualized and quantified using immunohistochemical methods and matrix-specific gene expression quantified by in situ mRNA hybridization.

Example 2

Preparation of Collagen-Based Matrix

This example illustrates another exemplary method for preparation of the collagen-based matrix.

300 grams of a 1% aqueous atelocollagen solution (VITROGEN®), maintained at pH 3.0, is poured into a 10×20 cm tray. This tray is then placed in a 5 liter container. A 50 mL open container containing 30 mL of a 3% aqueous ammonia solution is then placed next to the tray, in the 5 liter chamber, containing 300 grams of said 1% aqueous solution of atelocollagen. The 5 liter container containing the open trays of atelocollagen and ammonia is then sealed and left to stand at room temperature for 12 hours. During this period the ammonia gas, released from the open container of aqueous ammonia and confined within the sealed 5 liter container, is reacted with the aqueous atelocollagen resulting in gelling said aqueous solution of atelocollagen.

The collagenous gel is then washed with water overnight and, subsequently, freeze-dried to yield a sponge like matrix. This freeze dried matrix is then cut into squares, sterilized, and stored under a sterile wrap.

Example 3

Effect of Ammonia on Preparation of Porous Honeycomb Scaffold

This example illustrates a general procedure utilizing ammonia for preparation of porous honeycomb scaffold having substantially the same size and distribution of pores.

About 30 g collagen solution (concentrations listed in table 1) with a pH of 3.0-4.8 was added to a 100 ml glass beaker. The solution was centrifuged for 5-10 minutes at 800×g to remove air bubbles. After centrifugation the beaker with collagen solution was sealed in a 7.1 $dm^3$ container together with 3% aqueous ammonia. The collagen solution was precipitated in the presence of ammonia gas for 3-14 h, forming vertical cone shaped pores where the diameter increased with the depth. After precipitation the collagen gel was washed with deionized water for 1-3 days in order to remove excess ammonia and formed salts. The washed collagen was then slowly frozen and lyophilized.

Example 4

Effect of Surfactant on Pore Size

This example illustrates preparation of porous honeycomb scaffold in the presence of a surfactant.

20 g of collagen solution with 0.3 weight % of Pluronic® F68 (BASF), a non ionic surfactant with a pH of 3.5-3.8, was added to a 100 ml glass beaker. The collagen concentration versus the final pore size is listed in the table below. The solution was centrifuged for 5-10 minutes at 800×g to remove air bubbles. After centrifugation the beaker with collagen solution was sealed in a 7.1 $dm^3$ container together with 3% aqueous ammonia. The collagen solution was precipitated in the presence of ammonia gas for 2 h, forming vertical cone shaped pores where the diameter increased with the depth. After precipitation the collagen gel was washed with deionized water for 1 day in order to remove excess ammonia and formed salts. The washed collagen was then slowly frozen and lyophilized.

Example 5

Effect of Inert Atmosphere and Reduced Pressure on Pore Size

This example illustrates preparation of honeycomb porous scaffold in inert atmosphere ($N_2$) and under reduced pressure. 15 g of bovine type 1 atelocollagen dissolved in aqueous HCl with a concentration of 5 mg/ml and pH of 3.3 was added to a 100 ml glass beaker. The solution was centrifuged for 5-10 minutes at 800×g to remove air bubbles. After centrifugation the collagen solution was placed in 9.1 $dm^3$ container. The container was sealed and the air evacuated using a vacuum pump to a pressure of about 2 torr (water almost boiled). The pump was turned off and the system was filled with nitrogen to about 27 torr. Evacuation and filling was repeated three times. Before the addition of ammonia the pressure was again reduced to about 2 torr and the vacuum pump and flask were closed off. Aqueous ammonia was charged to the flask and after 30 seconds the connection to the container was opened and nitrogen was used to flush the ammonia gas into the container with the collagen solution. The final pressure in the container was in the range of 3-15 torr. The precipitation and formation of pores was complete in 40 minutes.

The formed pores were vertical and cone shaped and the diameter increased with increasing distance from the surface of the collagen gel. The precipitated collagen was washed with deionized water for 1 day in order to remove excess ammonia and formed salts. The washed collagen was then slowly frozen and lyophilized.

Example 6

Evaluation of Time-Dependent Production of Proteoglycan

This example describes a study performed for evaluation of the importance of the pore size for induction of production of a hyaline articulate cartilage.

To evaluate the effect of the pore size of through porous matrix, 2 different pore sized matrices were prepared. Large pore matrix had pores of an average size of 435 μm. Small pore matrix had pores of an average size of 153 μm.

Cells were harvested with trypsin-EDTA (Invitrogen). Three hundred thousand chondrocytes obtained from human articulate cartilage (hACs) were suspended in hydrogel (collagen gel) and seeded into a composite of a porous sponge matrix having an average pore size 435 μm or an average pore size 153 μm. The composites were then transferred into the culture medium. After 12 hours pre-incubation, cell constructs were cultured in medium comprising 5% $CO_2$. 2% $O_2$ and 37° C. in a multigas incubator using DMEM/F-12 medium with 10% FBS, 1% ITS, 0.1% gentamycin (Invitrogen). After 21 days of culture, constructs were harvested for biochemical evaluation.

Example 7

Biochemical Evaluations

This example describes methods used for biochemical evaluation of collagen-based composites.

For biochemical analysis, composites were digested in papain at 60° C. for 18 hours. DNA was measured using the Hoechst 33258 dye method described in *Anal. Biochem.*, 174:168-176 (1988) Sulfated-glycosaminoglycan (S-GAG) content was measured using a modified dimethylmethylene blue (DMB) microassay described in *Connect. Tissue Res.*, 9:247-248 (1982).

Example 8

Cell Seeding in a Three-Dimensional Collagen-Based Matrix

This example describes the procedure used for cell harvesting and seeding in the collagen-based matrix according to the invention.

Cells were harvested with trypsin-EDTA (Invitrogen). Three hundred thousand human articular chondrocytes (hACs) were suspended in a collagen hydrogel and seeded into the composite of porous collagen-based matrix having a predetermined average pore size 435 μm or 153 μm. The cell constructs were incubated at 37° C. for about one hour collagen gelation and then transferred into the culture medium. After 12 hours pre-incubation, the composites comprising chondrocytes were cultivated. After zero and 21 days of culture, constructs were harvested for biochemical evaluation.

Viability Determination

This example illustrates determination of cell viability.

Collagen-based matrices prepared by the surfactant method were seeded with approximately 200,000 chondrocytes in a collagen gel by absorption and incubated for 3 days. An n=3 was used for each group. At termination, the chondrocyte-contained matrices were placed in 15 ml microcentrifuge tubes and incubated overnight in 0.15% collagenase. The digest was spun at 2000 rpm for 5 minutes and the supernatant aspirated. An aliquot of culture medium (0.1 ml) was added to the cell pellets and an aliquot taken for counting. Cell viability and total cell count was measured using trypan blue.

What is claimed:

1. A collagen-based cell-support matrix having narrowly defined and uniformly vertically and non-randomly organized porosity and pore density wherein said matrix is prepared from a collagen-based biocompatible material, wherein said porosity is determined by pore size and wherein said pore size is substantially homogeneous in diameter.

2. The matrix of claim 1 wherein said biocompatible material comprises:
   (i) a collagen selected from the group consisting of Type I collagen, Type II collagen, and Type IV collagen, and
   (ii) optionally gelatin, agarose, hyaluronin, cell-contracted collagen containing proteoglycan, glycosaminoglycan, glycoprotein, fibronectin, laminin, bioactive peptide growth factors, cytokine, elastin, fibrin, synthetic polymeric fiber made of A poly-acid polylactic, polyglycolic, polyamino acid, polycaprolactone, polypeptide gel, a copolymer thereof, a precursor thereof and combination thereof, wherein said precursor is selected from the group consisting of alpha 1 (Type I) peptide, alpha 2 (Type I) peptide, 2 (alpha 1, Type I) peptide, 1 (alpha 2, Type I) peptide, 3 (alpha 1, Type II) and a combination thereof.

3. The matrix of claim 2 wherein said biocompatible material is Type I collagen.

4. The matrix of claim 3 wherein said pore size is set to be at least 95% homogeneous within a range of about 200±100 microns.

5. The matrix of claim 4 wherein said matrix is suitable as an acellular or a cellular implant for treatment and repair of articular cartilage injuries or damage.

6. The matrix of claim 4 wherein said matrix is suitable for an acellular or a cellular implant for treatment of connective tissue injuries.

7. The matrix of claim 4 wherein said matrix is suitable for in vitro production of a hyaline or hyaline-like cartilage, tendon, ligament or meniscus.

8. The matrix of claim 3 wherein said pore size is set to be at least 98% homogeneous within a range of about 200±100 microns.

9. A collagen-based support matrix having narrowly defined and uniformly vertically and non-randomly organized porosity and pore density wherein said matrix is prepared from a Type I collagen, wherein said porosity is determined by the pore size of about 200±100 microns and wherein said pore size is about 95% homogeneous.

10. The matrix of claim 9 seeded with a suspension of chondrocytes in a gel solution.

11. The matrix of claim 10 wherein said gel is collagen, a sol-gel or hydrogel.

12. The matrix of claim 11 wherein said sol-gel has a transition temperature from sol to gel about 37° C.

13. The matrix of claim 9 wherein said chondrocytes are seeded in cell density of from about 25,000 to about 300,000 cells per 25 microliters.

* * * * *